(12) United States Patent
Sartor et al.

(10) Patent No.: US 7,156,842 B2
(45) Date of Patent: *Jan. 2, 2007

(54) ELECTROSURGICAL PENCIL WITH IMPROVED CONTROLS

(75) Inventors: Joe Don Sartor, Longmont, CO (US); Arlen James Reschke, Boulder, CO (US); David Nichols Heard, Boulder, CO (US); Dale Francis Schmaltz, Fort Collins, CO (US); Ronald J. Podhajsky, Boulder, CO (US); Steven Paul Buysse, Longmont, CO (US); Mark Huseman, Broomfield, CO (US)

(73) Assignee: Sherwood Services AG, Schaffhausen (CH)

( * ) Notice: Subject to any disclaimer, the term of this patent is extended or adjusted under 35 U.S.C. 154(b) by 14 days.

This patent is subject to a terminal disclaimer.

(21) Appl. No.: 10/959,824

(22) Filed: Oct. 6, 2004

(65) Prior Publication Data

US 2005/0113824 A1 May 26, 2005

Related U.S. Application Data

(63) Continuation-in-part of application No. PCT/US03/37111, filed on Nov. 20, 2003.

(51) Int. Cl.
*A61B 18/18* (2006.01)
(52) U.S. Cl. .............................. 606/37; 606/45; 606/49
(58) Field of Classification Search ............ 606/37–42, 606/45–52
See application file for complete search history.

(56) References Cited

U.S. PATENT DOCUMENTS

| | | |
|---|---|---|
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Sr. |
| 3,648,001 A | 3/1972 | Anderson et al. |
| 3,675,655 A | 7/1972 | Sittner |
| 3,699,967 A | 10/1972 | Anderson |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,875,945 A | 4/1975 | Friedman |
| 3,902,494 A | 9/1975 | Haberlen et al. |
| 3,906,955 A | 9/1975 | Roberts |
| 3,967,084 A | 6/1976 | Pounds |
| 3,974,833 A | 8/1976 | Durden, III |
| 4,014,343 A | 3/1977 | Esty |
| 4,032,738 A | 6/1977 | Esty et al. |

(Continued)

FOREIGN PATENT DOCUMENTS

DE 24 29 021 A1 1/1976

(Continued)

OTHER PUBLICATIONS

International Search Report from PCT/US03/37111.

(Continued)

*Primary Examiner*—Michael Peffley

(57) ABSTRACT

An electrosurgical pencil is provided which includes an elongated housing, an electrocautery blade supported within the housing and extending distally from the housing. The electrocautery blade is connected to a source of electrosurgical energy. The pencil also includes at least one activation switch supported on the housing which is configured and adapted to complete a control loop extending from the source of electrosurgical energy. At least one voltage divider network is also supported on the housing and is electrically connected to the source of electrosurgical energy.

71 Claims, 15 Drawing Sheets

U.S. PATENT DOCUMENTS

| | | |
|---|---|---|
| 4,034,761 A | 7/1977 | Prater et al. |
| 4,038,984 A | 8/1977 | Sittner |
| 4,112,950 A | 9/1978 | Pike |
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |
| 4,545,375 A | 10/1985 | Cline |
| 4,562,838 A | 1/1986 | Walker |
| 4,589,411 A | 5/1986 | Friedman |
| 4,593,691 A | 6/1986 | Lindstrom et al. |
| 4,595,809 A | 6/1986 | Pool |
| 4,606,342 A | 8/1986 | Zamba et al. |
| 4,619,258 A | 10/1986 | Pool |
| 4,625,723 A | 12/1986 | Altnether et al. |
| 4,640,279 A | 2/1987 | Beard |
| 4,642,128 A | 2/1987 | Solorzano |
| 4,655,215 A | 4/1987 | Pike |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,712,544 A | 12/1987 | Ensslin |
| 4,735,603 A | 4/1988 | Goodson et al. |
| 4,754,754 A | 7/1988 | Garito et al. |
| 4,785,807 A | 11/1988 | Blanch |
| 4,788,977 A | 12/1988 | Farin et al. |
| 4,794,215 A | 12/1988 | Sawada et al. |
| 4,803,323 A | 2/1989 | Bauer et al. |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,846,790 A | 7/1989 | Hornlein et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,872,454 A | 10/1989 | DeOliveira et al. |
| 4,876,110 A | 10/1989 | Blanch |
| 4,886,060 A | 12/1989 | Wiksell |
| 4,901,719 A | 2/1990 | Trenconsky et al. |
| 4,903,696 A | 2/1990 | Stasz et al. |
| 4,909,249 A | 3/1990 | Akkas et al. |
| 4,911,159 A | 3/1990 | Johnson et al. |
| 4,916,275 A | 4/1990 | Almond |
| 4,919,129 A | 4/1990 | Weber, Jr. et al. |
| 4,921,476 A | 5/1990 | Wuchinich |
| 4,922,903 A | 5/1990 | Welch et al. |
| 4,931,047 A | 6/1990 | Broadwin et al. |
| 4,949,734 A | 8/1990 | Bernstein |
| 4,969,885 A | 11/1990 | Farin |
| 4,986,839 A | 1/1991 | Wertz et al. |
| 4,988,334 A | 1/1991 | Hornlein et al. |
| 5,000,754 A | 3/1991 | DeOliveira et al. |
| 5,011,483 A | 4/1991 | Sleister |
| 5,013,312 A | 5/1991 | Parins et al. |
| 5,015,227 A | 5/1991 | Broadwin et al. |
| 5,026,368 A | 6/1991 | Adair |
| 5,046,506 A | 9/1991 | Singer |
| 5,055,100 A | 10/1991 | Olsen |
| 5,071,418 A | 12/1991 | Rosenbaum |
| 5,074,863 A | 12/1991 | Dines |
| 5,076,276 A | 12/1991 | Sakurai et al. |
| 5,088,997 A | 2/1992 | Delahuerga et al. |
| 5,098,430 A | 3/1992 | Fleenor |
| 5,100,402 A | 3/1992 | Fan |
| 5,108,391 A | 4/1992 | Flachenecker et al. |
| 5,133,714 A | 7/1992 | Beane |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |
| 5,167,659 A | 12/1992 | Ohtomo et al. |
| 5,178,605 A | 1/1993 | Imonti |
| 5,190,517 A | 3/1993 | Zieve et al. |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | Delahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,234,429 A | 8/1993 | Goldhaber |
| 5,242,442 A | 9/1993 | Hirschfeld |
| 5,244,462 A | 9/1993 | Delahuerga et al. |
| 5,246,440 A | 9/1993 | Van Noord |
| 5,254,082 A | 10/1993 | Takase |
| 5,254,117 A | 10/1993 | Rigby et al. |
| 5,256,138 A | 10/1993 | Burek et al. |
| 5,261,906 A | 11/1993 | Pennino et al. |
| 5,269,781 A | 12/1993 | Hewell, III |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,312,400 A | 5/1994 | Bales et al. |
| 5,312,401 A | 5/1994 | Newton et al. |
| 5,318,516 A | 6/1994 | Cosmescu |
| 5,318,565 A | 6/1994 | Kuriloff et al. |
| 5,322,503 A | 6/1994 | Desai |
| 5,330,470 A | 7/1994 | Hagen |
| 5,334,183 A | 8/1994 | Wuchinich |
| 5,342,356 A | 8/1994 | Ellman et al. |
| 5,348,555 A | 9/1994 | Zinnanti |
| 5,376,089 A | 12/1994 | Smith |
| 5,380,320 A | 1/1995 | Morris |
| 5,382,247 A | 1/1995 | Cimino et al. |
| 5,395,363 A | 3/1995 | Billings et al. |
| 5,399,823 A | 3/1995 | McCusker |
| 5,401,273 A | 3/1995 | Shippert |
| 5,403,882 A | 4/1995 | Huggins |
| 5,406,945 A | 4/1995 | Riazzi et al. |
| 5,409,484 A | 4/1995 | Erlich et al. |
| 5,413,575 A | 5/1995 | Haenggi |
| 5,421,829 A | 6/1995 | Olichney et al. |
| 5,423,838 A | 6/1995 | Willard |
| 5,431,645 A | 7/1995 | Smith et al. |
| 5,431,650 A | 7/1995 | Cosmescu |
| 5,451,222 A | 9/1995 | De Maagd et al. |
| 5,460,602 A | 10/1995 | Shapira |
| 5,462,522 A | 10/1995 | Sakurai et al. |
| 5,468,240 A | 11/1995 | Gentelia et al. |
| 5,472,442 A | 12/1995 | Klicek |
| 5,472,443 A | 12/1995 | Cordis et al. |
| 5,484,398 A | 1/1996 | Stoddard |
| 5,484,434 A | 1/1996 | Cartmell et al. |
| 5,486,162 A | 1/1996 | Brumbach |
| 5,496,314 A | 3/1996 | Eggers |
| 5,498,654 A | 3/1996 | Shimasaki et al. |
| D370,731 S | 6/1996 | Corace et al. |
| 5,531,722 A | 7/1996 | Van Hale |
| 5,549,604 A | 8/1996 | Sutcu et al. |
| 5,561,278 A | 10/1996 | Rutten |

| Patent | Date | Inventor |
|---|---|---|
| 5,601,224 A | 2/1997 | Bishop et al. |
| 5,609,573 A | 3/1997 | Sandock |
| 5,626,575 A | 5/1997 | Crenner |
| 5,630,426 A | 5/1997 | Eggers et al. |
| 5,630,812 A | 5/1997 | Ellman et al. |
| 5,633,578 A | 5/1997 | Eggers et al. |
| 5,634,912 A | 6/1997 | Injev |
| 5,643,256 A | 7/1997 | Urueta |
| D384,148 S | 9/1997 | Monson |
| 5,669,907 A | 9/1997 | Platt, Jr. et al. |
| 5,674,219 A | 10/1997 | Monson et al. |
| 5,693,044 A | 12/1997 | Cosmescu |
| 5,693,050 A | 12/1997 | Speiser |
| 5,693,052 A | 12/1997 | Weaver |
| 5,697,926 A | 12/1997 | Weaver |
| 5,702,360 A | 12/1997 | Dieras et al. |
| 5,702,387 A | 12/1997 | Arts et al. |
| 5,712,543 A | 1/1998 | Sjostrom |
| 5,713,895 A | 2/1998 | Lontine et al. |
| 5,720,745 A | 2/1998 | Farin et al. |
| D393,067 S | 3/1998 | Geary et al. |
| 5,749,869 A | 5/1998 | Lindenmeier et al. |
| 5,765,418 A | 6/1998 | Rosenberg |
| 5,776,092 A | 7/1998 | Farin et al. |
| 5,788,688 A | 8/1998 | Bauer et al. |
| 5,797,907 A | 8/1998 | Clement |
| 5,800,431 A | 9/1998 | Brown |
| 5,836,897 A | 11/1998 | Sakurai et al. |
| 5,836,909 A | 11/1998 | Cosmescu |
| 5,836,944 A | 11/1998 | Cosmescu |
| D402,030 S | 12/1998 | Roberts et al. |
| D402,031 S | 12/1998 | Roberts et al. |
| 5,843,109 A | 12/1998 | Mehta et al. |
| 5,846,236 A | 12/1998 | Lindenmeier et al. |
| 5,859,527 A | 1/1999 | Cook |
| 5,868,768 A | 2/1999 | Wicherski et al. |
| 5,876,400 A | 3/1999 | Songer |
| 5,888,200 A | 3/1999 | Walen |
| 5,893,848 A | 4/1999 | Negus et al. |
| 5,893,849 A | 4/1999 | Weaver |
| 5,893,862 A | 4/1999 | Pratt et al. |
| 5,913,864 A | 6/1999 | Garito et al. |
| 5,919,219 A | 7/1999 | Knowlton |
| 5,928,159 A | 7/1999 | Eggers et al. |
| 5,941,887 A | 8/1999 | Steen et al. |
| 5,944,737 A | 8/1999 | Tsonton et al. |
| 5,951,548 A | 9/1999 | DeSisto et al. |
| 5,951,581 A | 9/1999 | Saadat et al. |
| 5,954,686 A | 9/1999 | Garito et al. |
| 5,972,007 A | 10/1999 | Sheffield et al. |
| 6,004,318 A | 12/1999 | Garito et al. |
| 6,004,333 A | 12/1999 | Sheffield et al. |
| 6,004,335 A | 12/1999 | Vaitekunas et al. |
| 6,010,499 A | 1/2000 | Cobb |
| 6,022,347 A | 2/2000 | Lindenmeier et al. |
| 6,045,564 A | 4/2000 | Walen |
| 6,063,050 A | 5/2000 | Manna et al. |
| 6,068,627 A | 5/2000 | Orszulak et al. |
| 6,070,444 A | 6/2000 | Lontine et al. |
| 6,071,281 A | 6/2000 | Burnside et al. |
| 6,074,386 A | 6/2000 | Goble et al. |
| 6,074,387 A | 6/2000 | Heim et al. |
| 6,086,544 A | 7/2000 | Hibner et al. |
| 6,090,123 A | 7/2000 | Culp et al. |
| 6,099,525 A | 8/2000 | Cosmescu |
| 6,117,134 A | 9/2000 | Cunningham et al. |
| 6,139,547 A | 10/2000 | Lontine et al. |
| D433,752 S | 11/2000 | Saravia |
| 6,142,995 A | 11/2000 | Cosmescu |
| 6,146,353 A | 11/2000 | Platt, Jr. |
| 6,149,648 A | 11/2000 | Cosmescu |
| 6,156,035 A | 12/2000 | Songer |
| 6,197,024 B1 | 3/2001 | Sullivan |
| 6,200,311 B1 | 3/2001 | Danek et al. |
| D441,077 S | 4/2001 | Garito et al. |
| 6,213,999 B1 | 4/2001 | Platt, Jr. et al. |
| 6,214,003 B1 | 4/2001 | Morgan et al. |
| 6,238,388 B1 * | 5/2001 | Ellman et al. ............ 606/37 |
| 6,241,723 B1 | 6/2001 | Heim et al. |
| 6,241,753 B1 | 6/2001 | Knowlton |
| 6,249,706 B1 | 6/2001 | Sobota et al. |
| 6,251,110 B1 | 6/2001 | Wampler |
| 6,257,241 B1 | 7/2001 | Wampler |
| 6,258,088 B1 | 7/2001 | Tzonev et al. |
| 6,273,862 B1 | 8/2001 | Privitera et al. |
| 6,277,083 B1 | 8/2001 | Eggers et al. |
| 6,287,305 B1 | 9/2001 | Heim et al. |
| 6,287,344 B1 | 9/2001 | Wampler et al. |
| 6,312,441 B1 | 11/2001 | Deng |
| 6,325,799 B1 | 12/2001 | Goble |
| D453,222 S | 1/2002 | Garito et al. |
| D453,833 S | 2/2002 | Hess |
| 6,350,276 B1 | 2/2002 | Knowlton |
| 6,355,034 B1 | 3/2002 | Cosmescu |
| 6,358,281 B1 | 3/2002 | Berrang et al. |
| 6,361,532 B1 | 3/2002 | Burek |
| D457,955 S | 5/2002 | Bilitz |
| 6,395,001 B1 | 5/2002 | Ellman et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,725 B1 | 6/2002 | Khandkar et al. |
| 6,413,255 B1 | 7/2002 | Stern |
| 6,416,491 B1 | 7/2002 | Edwards et al. |
| 6,416,509 B1 | 7/2002 | Goble et al. |
| 6,425,912 B1 | 7/2002 | Knowlton |
| 6,458,122 B1 | 10/2002 | Pozzato |
| 6,458,125 B1 | 10/2002 | Cosmescu |
| 6,461,352 B1 | 10/2002 | Morgan et al. |
| 6,464,702 B1 | 10/2002 | Schulze et al. |
| 6,471,659 B1 | 10/2002 | Eggers et al. |
| 6,494,882 B1 | 12/2002 | Lebouitz et al. |
| 6,500,169 B1 | 12/2002 | Deng |
| 6,511,479 B1 | 1/2003 | Gentelia et al. |
| 6,551,313 B1 | 4/2003 | Levin |
| 6,558,383 B1 | 5/2003 | Cunningham et al. |
| 6,585,664 B1 | 7/2003 | Burdorff et al. |
| 6,589,239 B1 | 7/2003 | Khandkar et al. |
| 6,610,054 B1 | 8/2003 | Edwards et al. |
| 6,610,057 B1 | 8/2003 | Ellman et al. |
| 6,616,658 B1 | 9/2003 | Ineson |
| 6,618,626 B1 | 9/2003 | West, Jr. et al. |
| 6,620,161 B1 | 9/2003 | Schulze et al. |
| 6,632,193 B1 | 10/2003 | Davison et al. |
| 6,652,514 B1 * | 11/2003 | Ellman et al. ............ 606/37 |
| 6,662,053 B1 | 12/2003 | Borkan |
| 6,669,691 B1 | 12/2003 | Taimisto |
| 6,685,701 B1 | 2/2004 | Orszulak et al. |
| 6,685,704 B1 | 2/2004 | Greep |
| 6,702,812 B1 | 3/2004 | Cosmescu |
| 6,712,813 B1 | 3/2004 | Ellman et al. |
| 6,740,079 B1 | 5/2004 | Eggers et al. |
| 6,747,218 B1 | 6/2004 | Huseman et al. |
| D493,530 S | 7/2004 | Reschke |
| D493,888 S | 8/2004 | Reschke |
| D494,270 S | 8/2004 | Reschke |
| D495,051 S | 8/2004 | Reschke |
| D495,052 S | 8/2004 | Reschke |
| 6,794,929 B1 | 9/2004 | Pelly |
| 6,830,569 B1 | 12/2004 | Thompson et al. |
| 6,840,948 B1 | 1/2005 | Albrecht et al. |
| 6,855,140 B1 | 2/2005 | Albrecht et al. |
| 6,902,536 B1 | 6/2005 | Manna et al. |
| 6,905,496 B1 | 6/2005 | Ellman et al. |
| 6,923,804 B1 | 8/2005 | Eggers et al. |

| | | |
|---|---|---|
| 6,923,809 B1 | 8/2005 | Eggers et al. |
| 6,939,347 B1 | 9/2005 | Thompson |
| 6,955,674 B1 | 10/2005 | Eick et al. |
| 2001/0047183 A1 | 11/2001 | Privitera et al. |
| 2001/0049524 A1 | 12/2001 | Morgan et al. |
| 2002/0019596 A1 | 2/2002 | Eggers et al. |
| 2002/0019631 A1 | 2/2002 | Kidder et al. |
| 2002/0022838 A1 | 2/2002 | Cunningham et al. |
| 2002/0035364 A1 | 3/2002 | Schoenman et al. |
| 2002/0049427 A1 | 4/2002 | Wiener et al. |
| 2002/0058958 A1 | 5/2002 | Walen |
| 2002/0087079 A1 | 7/2002 | Culp et al. |
| 2002/0095199 A1 | 7/2002 | West, Jr. et al. |
| 2002/0103485 A1 | 8/2002 | Melnyk et al. |
| 2002/0111622 A1 | 8/2002 | Khandkar et al. |
| 2002/0151887 A1 | 10/2002 | Stern et al. |
| 2002/0156471 A1 | 10/2002 | Stern et al. |
| 2002/0173776 A1 | 11/2002 | Batchelor et al. |
| 2002/0198519 A1 | 12/2002 | Qin et al. |
| 2003/0004508 A1 | 1/2003 | Morgan et al. |
| 2003/0014043 A1 | 1/2003 | Henry et al. |
| 2003/0032950 A1 | 2/2003 | Altshuler et al. |
| 2003/0050633 A1 | 3/2003 | Ellman et al. |
| 2003/0065321 A1 | 4/2003 | Carmel et al. |
| 2003/0078572 A1 | 4/2003 | Pearson et al. |
| 2003/0083655 A1 | 5/2003 | Van Wyk |
| 2003/0088247 A1 | 5/2003 | Ineson |
| 2003/0109864 A1 | 6/2003 | Greep et al. |
| 2003/0109865 A1 | 6/2003 | Greep et al. |
| 2003/0130663 A1 | 7/2003 | Walen |
| 2003/0144680 A1 | 7/2003 | Kellogg et al. |
| 2003/0163125 A1 | 8/2003 | Greep |
| 2003/0199856 A1 | 10/2003 | Hill et al. |
| 2003/0199866 A1 | 10/2003 | Stern et al. |
| 2003/0199869 A1 | 10/2003 | Johnson et al. |
| 2003/0212393 A1 | 11/2003 | Knowlton et al. |
| 2003/0212397 A1 | 11/2003 | Avrahami et al. |
| 2003/0216728 A1 | 11/2003 | Stern et al. |
| 2003/0220635 A1 | 11/2003 | Knowlton et al. |
| 2003/0220638 A1 | 11/2003 | Metzger |
| 2003/0225401 A1 | 12/2003 | Eggers et al. |
| 2003/0229341 A1 | 12/2003 | Albrecht et al. |
| 2003/0229343 A1 | 12/2003 | Albrecht et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0010246 A1 | 1/2004 | Takahashi |
| 2004/0015160 A1 | 1/2004 | Lovewell |
| 2004/0015161 A1 | 1/2004 | Lovewell |
| 2004/0015162 A1 | 1/2004 | McGaffigan |
| 2004/0015216 A1 | 1/2004 | DeSisto |
| 2004/0024395 A1 | 2/2004 | Ellman et al. |
| 2004/0024396 A1 | 2/2004 | Eggers |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0034346 A1 | 2/2004 | Stern et al. |
| 2004/0054370 A1 | 3/2004 | Given |
| 2004/0092927 A1 | 5/2004 | Podhajsky et al. |
| 2004/0111087 A1 | 6/2004 | Stern et al. |
| 2004/0124964 A1 | 7/2004 | Yulun et al. |
| 2004/0127889 A1 | 7/2004 | Zhang et al. |
| 2004/0143677 A1 | 7/2004 | Pavel |
| 2004/0147909 A1 | 7/2004 | Johnston et al. |
| 2004/0162553 A1 | 8/2004 | Peng et al. |
| 2004/0167512 A1 | 8/2004 | Stoddard et al. |
| 2004/0172011 A1 | 9/2004 | Yulun et al. |
| 2004/0172015 A1 | 9/2004 | Novak |
| 2004/0172016 A1 | 9/2004 | Bek et al. |
| 2004/0181140 A1 | 9/2004 | Falwell et al. |
| 2004/0230262 A1 | 11/2004 | Sartor et al. |
| 2004/0236323 A1 | 11/2004 | Schoenman et al. |
| 2004/0243120 A1 | 12/2004 | Orszulak et al. |
| 2004/0267252 A1 | 12/2004 | Washington et al. |
| 2004/0267254 A1 | 12/2004 | Manzo et al. |
| 2004/0267297 A1 | 12/2004 | Malackowski |
| 2005/0033286 A1 | 2/2005 | Eggers et al. |
| 2005/0059967 A1 | 3/2005 | Breazeale, Jr. et al. |
| 2005/0065510 A1 | 3/2005 | Carmel et al. |
| 2005/0070891 A1 | 3/2005 | De Sisto |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0107782 A1 | 5/2005 | Reschke |
| 2005/0113817 A1 | 5/2005 | Isaacson et al. |
| 2005/0113818 A1 | 5/2005 | Sartor et al. |
| 2005/0113823 A1 | 5/2005 | Reschke et al. |
| 2005/0113824 A1 | 5/2005 | Sartor et al. |
| 2005/0113825 A1 | 5/2005 | Cosmescu |
| 2005/0149001 A1 | 7/2005 | Akinobu et al. |
| 2005/0154385 A1 | 7/2005 | Heim et al. |
| 2006/0041257 A1 | 2/2006 | Sartor et al. |
| 2006/0058783 A1 | 3/2006 | Buchman |

FOREIGN PATENT DOCUMENTS

| | | |
|---|---|---|
| DE | 304596 | 7/1982 |
| EP | 0 186 369 A | 7/1986 |
| EP | 1050277 | 11/2000 |
| EP | 1050279 | 11/2000 |
| EP | 1082945 | 3/2001 |
| EP | 1293171 | 3/2003 |
| FR | 2235669 | 1/1975 |
| WO | WO94/20032 | 9/1994 |
| WO | WO 96/39086 | 12/1996 |
| WO | WO 01 64122 | 9/2001 |
| WO | WO 2002/47568 A1 | 6/2002 |
| WO | WO 2004/010883 A1 | 2/2004 |
| WO | WO 2004/073753 A2 | 9/2004 |
| WO | WO 2005/060849 A1 | 7/2005 |

OTHER PUBLICATIONS

International Search Report from PCT/US04/04685.
International Search Report from EP/0401/5980.
International Search Report from PCT/US03/22900.
Copy of ISR from EP 05019882.9 dated Feb. 16, 2006.
Copy of ISR from EP 05021777.7 dated Feb. 23, 2006.

* cited by examiner

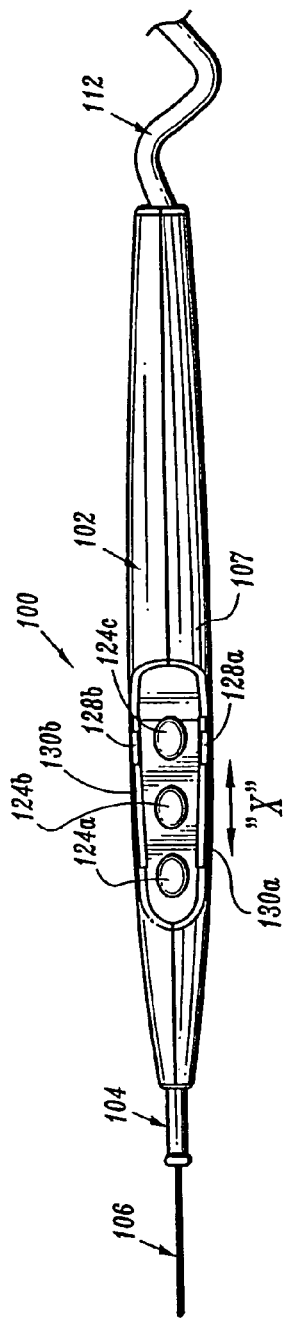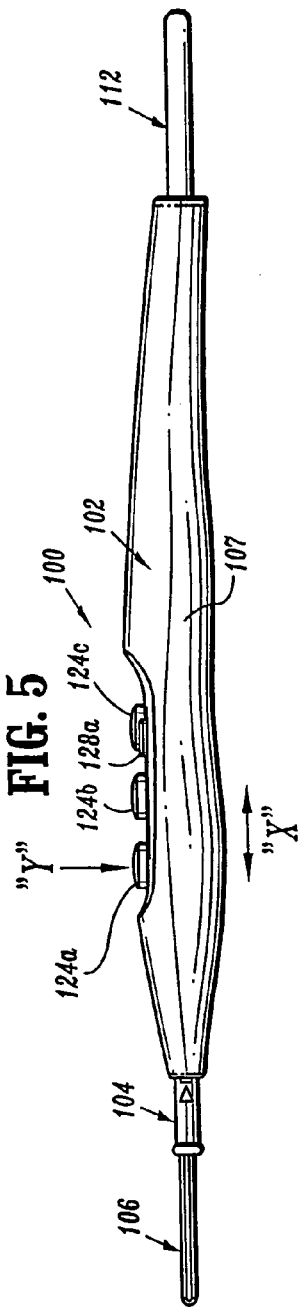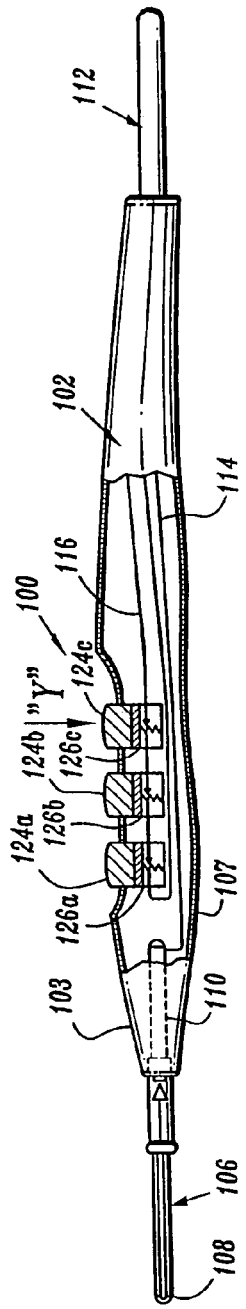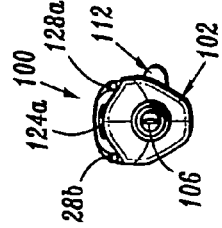

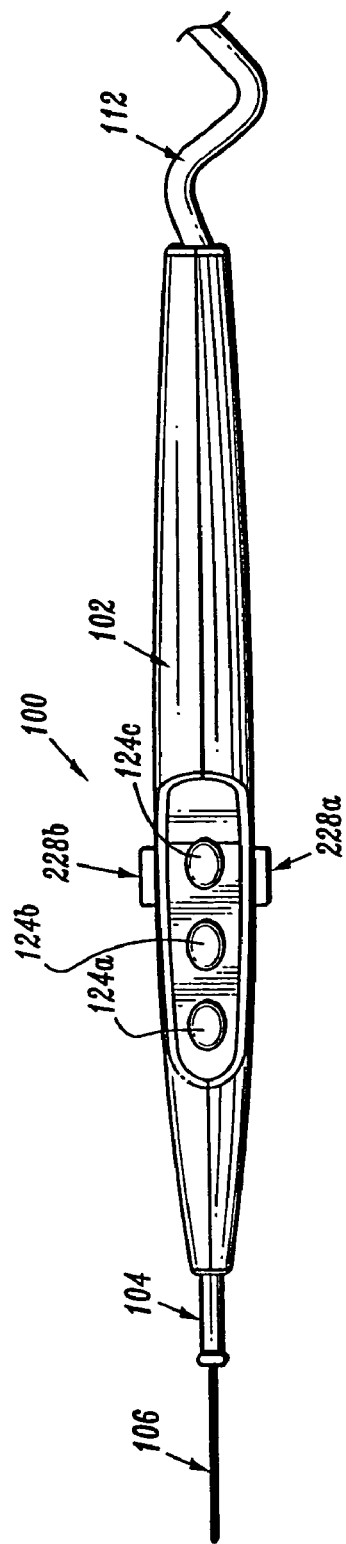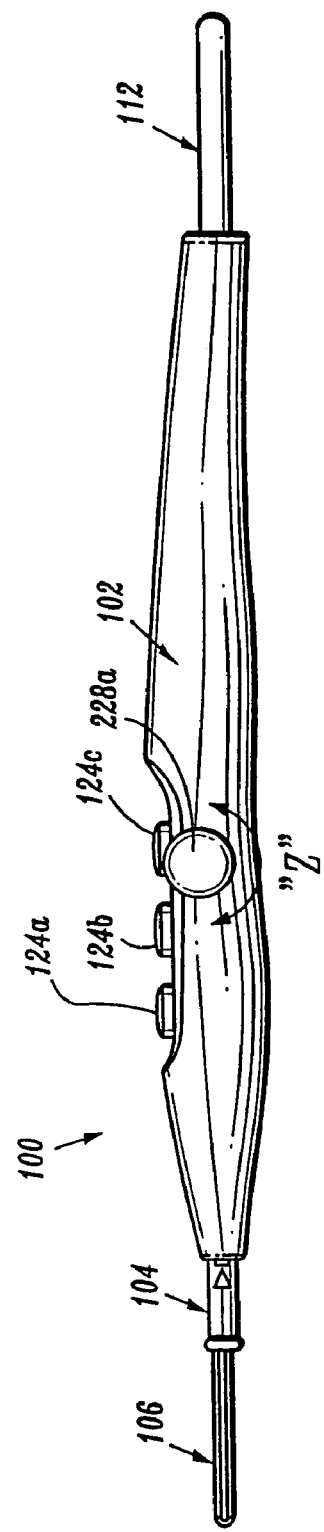
FIG. 9
FIG. 10

Note: Actual Power and Current ranges/settings may vary.
Mode 1 = Cut activation
Mode 2 = Division w/hemostasis activation
Mode 3 = Coag activation (Power Table / Units in Watts)

| Mode1 | 1 Bar | 2 Bar | 3 Bar | 4 Bar | 5 Bar | Mode2 | 1 Bar | 2 Bar | 3 Bar | 4 Bar | 5 Bar | Mode3 | 1 Bar | 2 Bar | 3 Bar | 4 Bar | 5 Bar |
|---|---|---|---|---|---|---|---|---|---|---|---|---|---|---|---|---|---|
| Slider Position 5 | 150 | 188 | 225 | 263 | 300 | Slider Position 5 | 100 | 125 | 150 | 175 | 200 | Slider Position 5 | 60 | 75 | 90 | 105 | 120 |
| Slider Position 4 | 113 | 150 | 188 | 225 | 263 | Slider Position 4 | 75 | 100 | 125 | 150 | 175 | Slider Position 4 | 45 | 60 | 75 | 90 | 105 |
| Slider Position 3 | 75 | 113 | 150 | 188 | 225 | Slider Position 3 | 50 | 75 | 100 | 125 | 150 | Slider Position 3 | 30 | 45 | 60 | 75 | 90 |
| Slider Position 2 | 38 | 75 | 113 | 150 | 188 | Slider Position 2 | 25 | 50 | 75 | 100 | 125 | Slider Position 2 | 15 | 30 | 45 | 60 | 75 |
| Slider Position 1 | 1 | 38 | 75 | 113 | 150 | Slider Position 1 | 1 | 25 | 50 | 75 | 100 | Slider Position 1 | 1 | 15 | 30 | 45 | 60 |

Example: If 2 Bar is selected and the slider is in position 4, then the value in that cell coordinate for each mode table is selected. Which are 150, 100, and 60 Watts in this example.

FIG. 19

(Current Table / Units in Amps)

| | Mode1 | 1 Bar | 2 Bar | 3 Bar | 4 Bar | 5 Bar | Mode2 | 1 Bar | 2 Bar | 3 Bar | 4 Bar | 5 Bar | Mode3 | 1 Bar | 2 Bar | 3 Bar | 4 Bar | 5 Bar |
|---|---|---|---|---|---|---|---|---|---|---|---|---|---|---|---|---|---|---|
| Slider Position 5 | | .625 | .782 | .938 | 1.09 | 1.25 | Slider Position 5 | .500 | .625 | .750 | .880 | 1.0 | Slider Position 5 | .500 | .625 | .750 | .880 | 1.0 |
| Slider Position 4 | | .470 | .625 | .782 | .938 | 1.09 | Slider Position 4 | .380 | .500 | .625 | .750 | .880 | Slider Position 4 | .380 | .500 | .625 | .750 | .880 |
| Slider Position 3 | | .313 | .470 | .625 | .782 | .938 | Slider Position 3 | .250 | .380 | .500 | .625 | .750 | Slider Position 3 | .250 | .380 | .500 | .625 | .750 |
| Slider Position 2 | | .157 | .313 | .470 | .625 | .782 | Slider Position 2 | .130 | .250 | .380 | .500 | .625 | Slider Position 2 | .130 | .250 | .380 | .500 | .625 |
| Slider Position 1 | | .001 | .157 | .313 | .470 | .625 | Slider Position 1 | .001 | .130 | .250 | .380 | .500 | Slider Position 1 | .001 | .130 | .250 | .380 | .500 |

Example: If 2 Bar is selected and the slider is in position Index 4 and Mode 1 is selected, then the value in that mode table and cell coordinate is selected. Which is .625A, .500A, and .500A for this example.

FIG. 20

(Output Table / Units in Amps)

| Output | Mode 1 | Mode 2 | Mode 3 |
|---|---|---|---|
| Frequency (kHz) | 473kHz | 473kHz @ 27kHz | 473kHz @ 27kHz |
| Duty Cycle | 100% | 25% | 8% |

|  | Mode 1 | Mode 2 | Mode 3 |
|---|---|---|---|
| Slider Position 5 | .782 | .625 | .625 |
| Slider Position 4 | .625 | .500 | .500 |
| Slider Position 3 | .470 | .380 | .380 |
| Slider Position 2 | .313 | .250 | .250 |
| Slider Position 1 | .157 | .130 | .130 |

FIG. 21

(Mode and Power Display / Units in Watts)

| MODE | Power (Watts) |
|---|---|
| CUT | 150 |
| DIVIDE | 100 |
| COAG | 60 |

FIG. 22

ELECTROSURGICAL PENCIL WITH IMPROVED CONTROLS

CROSS-REFERENCE TO RELATED APPLICATIONS

The present application is a continuation-in-part Application claiming benefit of and priority to International Application No. PCT/US03/37111, filed on Nov. 20, 2003, the entire content of which is incorporated herein by reference.

BACKGROUND

1. Technical Field

The present disclosure relates generally to electrosurgical instruments and, more particularly, to an electrosurgical pencil having a plurality of hand-accessible variable controls.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

In particular, electrosurgical fulguration includes the application of electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments which have a handpiece which is attached to an active electrode and which is used to cauterize, coagulate and/or cut tissue. Typically, the electrosurgical pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

A typical electrosurgical generator has numerous controls for selecting an electrosurgical output. For example, the surgeon can select various surgical "modes" to treat tissue: cut, blend (blend levels 1–3), low cut, desiccate, fulgurate, spray, etc. The surgeon also has the option of selecting a range of power settings typically ranging from 1–300 W. As can be appreciated, this gives the surgeon a great deal of variety when treating tissue. However, so many options also tend to complicate simple surgical procedures and may lead to confusion. Moreover, surgeons typically follow preset control parameters and stay within known modes and power settings. Therefore, there exists a need to allow the surgeon to selectively control and easily select and regulate the various modes and power settings utilizing simple and ergonomically friendly controls associated with the electrosurgical pencil.

Existing electrosurgical instrument systems allow the surgeon to change between two pre-configured settings (i.e., coagulation and cutting) via two discrete switches disposed on the electrosurgical pencil itself. Other electrosurgical instrument systems allow the surgeon to increment the power applied when the coagulating or cutting switch of the instrument is depressed by adjusting or closing a switch on the electrosurgical generator. The surgeon then needs to visually verify the change in the power being applied by looking at various displays and/or meters on the electrosurgical generator. In other words, all of the adjustments to the electrosurgical instrument and parameters being monitored during the use of the electrosurgical instrument are typically located on the electrosurgical generator. As such, the surgeon must continually visually monitor the electrosurgical generator during the surgical procedure.

Accordingly, the need exists for electrosurgical instruments which do not require the surgeon to continually monitor the electrosurgical generator during the surgical procedure. In addition, the need exists for electrosurgical instruments which may be configured such that the power output can be adjusted without the surgeon having to turn his/her vision away from the operating site and toward the electrosurgical generator.

SUMMARY

The present disclosure is directed to an electrosurgical pencil having variable controls. In accordance with one aspect of the present disclosure the electrosurgical pencil includes an elongated housing and an electrocautery blade supported within the housing and extending distally from the housing. The electrocautery blade is, in turn, connected to a source of electrosurgical energy. The pencil also includes a plurality of activation switches supported on the housing. Each activation switch is configured and adapted to selectively complete a control loop extending from the source of electrosurgical energy upon actuation thereof. At least one voltage divider network is also supported on the housing. The voltage divider network (hereinafter "VDN") is electrically connected to the source of electrosurgical energy and controls the intensity of electrosurgical energy being delivered to the plurality of activation switches.

The VDN preferably includes at least a return control wire is provided for electrically inter-connecting the electrocautery electrode and the source of electrosurgical energy. The return control wire transmits excess electrosurgical energy from the electrocautery electrode to the source of electrosurgical energy.

The VDN may further include a plurality of control wires for electrically inter-connecting a respective activation switch to the source of electrosurgical energy. Each control wire delivers electrosurgical energy from the source of electrosurgical energy to the electrocautery electrode.

Desirably, the voltage network divider includes a slide potentiometer operatively associated with the housing. The slide potentiometer simultaneously controls the intensity of electrosurgical energy delivered to the plurality of activation switches.

The plurality of activation switches define a first resistor network disposed within the housing and the slide potentiometer defines a second resistor network disposed within the housing.

It is envisioned that the voltage divider network may include an algorithm which stores the last setting for each activation switch. It is further envisioned that the voltage divider network may include an algorithm which requires the slide potentiometer to be set to zero each time the mode of operation of the electrosurgical pencil is changed.

The activation switch or switches is/are preferably configured and adapted to control a waveform duty cycle to achieve a desired surgical intent. Additional switches may be utilized to control the so-called "mode" of operation, i.e., cut, coagulate, blend, and/or may be utilized to control the intensity/power.

It is envisioned that the electrosurgical pencil includes three mode activation switches supported on the housing. Each mode activation switch preferably delivers a characteristic signal to the source of electrosurgical energy which, in turn, transmits a corresponding waveform duty cycle to the electrosurgical pencil. It is contemplated that a first activation switch delivers a first characteristic signal to the source of electrosurgical energy which, in turn, transmits a waveform duty cycle which produces a cutting effect. The second activation switch delivers a second characteristic signal to the source of electrosurgical energy which, in turn, transmits a waveform duty cycle which produces a blending effect. The third activation switch delivers a third characteristic signal to the source of electrosurgical energy which, in turn, transmits a waveform duty cycle which produces a coagulating effect.

It is envisioned that a single VDN may be supported on the housing. The VDN is preferably configured and adapted to adjust the intensity or power of the waveform duty cycle corresponding to a particular activation switch. The VDN advantageously includes a plurality of intensity settings. For typical monopolar applications, the VDN may be configured and adapted to vary the current intensity at 2K ohms from a minimum of about 60 mA to a maximum of about 240 mA, and more preferably, from a minimum of about 100 mA to a maximum of about 200 mA at 2K ohms.

The VDN can be slidably supported on the housing. As such, the VDN is set to a minimum when the VDN is placed at a first position, e.g., distal-most, and is set to a maximum when the VDN is placed at a second position, proximal-most or vice versa. The VDN is also positionable at varying places therebetween. The VDN may also be configured and adapted to provide a plurality of incremental (i.e., discreet) intensity settings or may be variable through a range. Alternatively, the VDN may be rotatably supported on the housing.

It is envisioned that the electrode may be a blade, needle, loop or ball. It is also envisioned that the VDN may be a slide potentiometer and include a pair of nubs slidably supported, one each, on either side of the plurality of activation switches, wherein the potentiometer is operable from either side of the electrosurgical instrument for use by ambidextrous users.

It is further envisioned that the housing may include a recess formed in the outer surface thereof, and wherein the plurality of activation switches and the nubs of the at least one voltage divider network are disposed within the recess.

Desirably, the electrosurgical pencil includes a molded hand grip operatively supported on the housing. The hand grip is preferably shaped and dimensioned to reduce fatigue on the hand of the user.

According to another aspect of the present disclosure, an electrosurgical pencil is provide and includes an elongate housing and an electrocautery end effector supported within the housing and extending distally from the housing. The electrosurgical pencil also includes a plurality of activation switches supported on the housing, wherein each activation switch is configured and adapted to energize the end effector with electrosurgical energy. The pencil still further includes at least one VDN supported on the housing which is configured and adapted to control the intensity of the electrosurgical energy being delivered to the electrocautery blade.

Each activation switch is configured and adapted to energize the end effector with a waveform duty cycle to achieve a desired surgical intent. Preferably, the electrosurgical pencil includes three mode activation switches supported on the housing, wherein each of the three mode activation switches is configured and adapted to deliver a characteristic signal (voltage or current level, impedance, capacitance, inductance and/or frequency) to a source of electrosurgical energy which source of electrosurgical energy in turn transmits a corresponding waveform duty cycle to the end effector. A first activation switch activates a waveform duty cycle which produces a dissecting effect, a second activation switch activates a waveform duty cycle which produces a dissecting and hemostatic effect, and a third activation switch activates a waveform duty cycle which produces a hemostatic effect. These effects have been typically referred to as cut, blend, and coagulation effects or modes.

It is envisioned that the VDN may include a pair of nubs slidably supported on the housing, one each, on either side of the activation switches. It is also contemplated that the VDN may be configured as a rheostat wherein, the VDN has a first position corresponding to a minimum intensity, a second position corresponding to a maximum intensity and a plurality of other positions corresponding to intensities between the minimum and the maximum intensity.

It is contemplated that the waveform duty cycle of the activation switches varies with a change in intensity produced by the VDN.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

FIG. 5 is a top plan view of the electrosurgical pencil of FIG. 4;

FIG. 6 is a side elevational view of the electrosurgical pencil of FIGS. 4 and 5;

FIG. 7 is a partially broken away, side elevational view of the electrosurgical pencil of FIGS. 4–6;

FIG. 8 is a front elevational view of the electrosurgical pencil of FIGS. 4–7;

FIG. 9 is a side elevational view of an electrosurgical pencil according to another embodiment of the present disclosure;

FIG. 10 is a top plan view of the electrosurgical pencil of FIG. 9;

FIG. 19 is a power setting look-up table for the electrosurgical generator of FIG. 17, for use with the electrosurgical pencil of FIGS. 1–3;

FIG. 20 is an electrical current look-up table for the electrosurgical generator of FIG. 17, for use with the electrosurgical pencil of FIGS. 1–3;

FIG. 21 is an output look-up table for the electrosurgical generator of FIG. 17, for use with the electrosurgical pencil of FIGS. 1–3; and FIG. 22 is a Mode and Power Display versus Power for the electrosurgical generator of FIG. 17, for use with the electrosurgical pencil of FIGS. 1–3.

DETAILED DESCRIPTION

Figure 1:
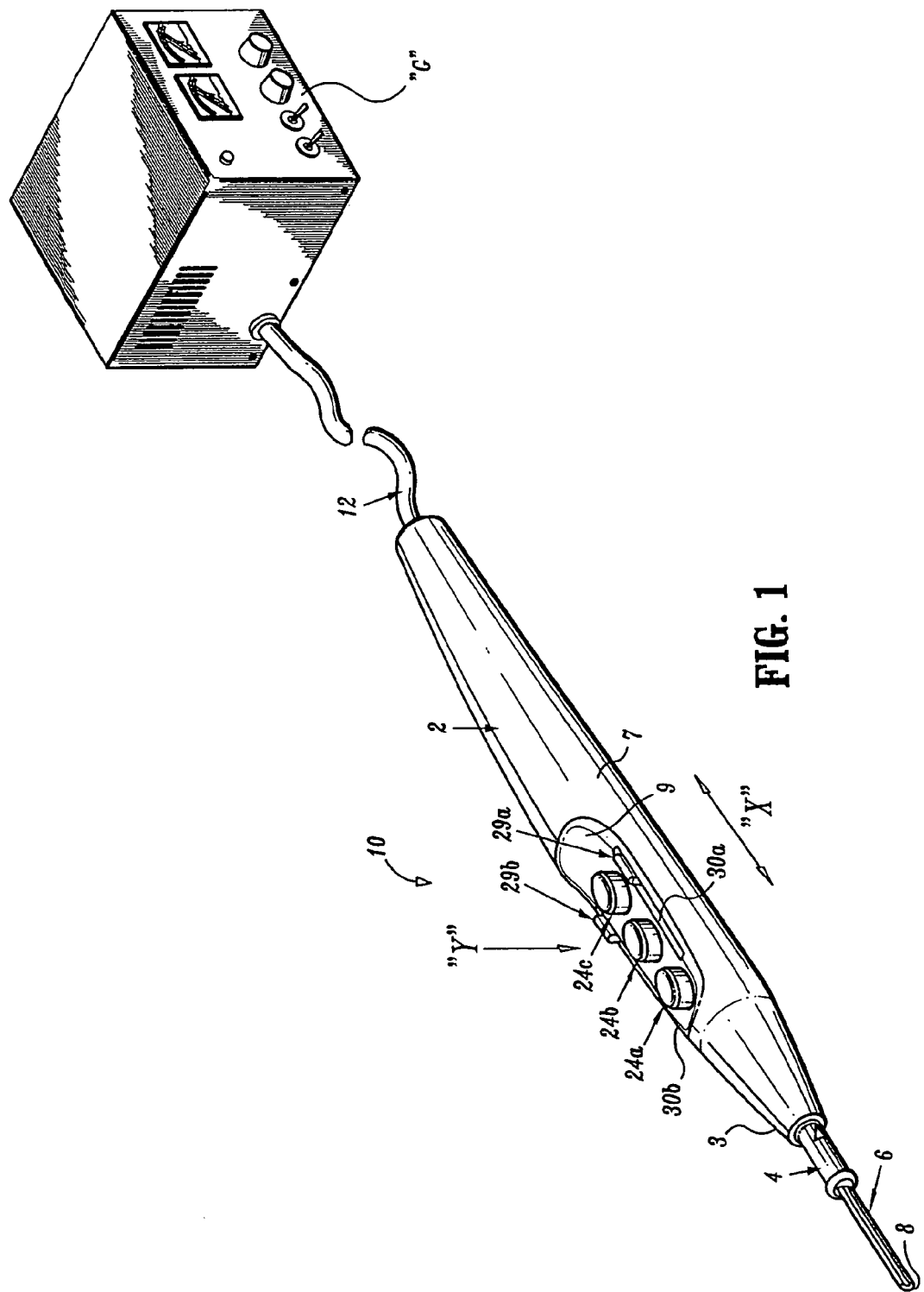
FIG. 1 is a perspective view of an electrosurgical pencil in accordance with the present disclosure.

Preferred embodiments of the presently disclosed electrosurgical pencil will now be described in detail with reference to the drawing figures wherein like reference numerals identify similar or identical elements. As used herein, the term "distal" refers to that portion which is further from the user while the term "proximal" refers to that portion which is closer to the user or surgeon.

FIG. 1 sets forth a perspective view of an electrosurgical pencil constructed in accordance with one embodiment of the present disclosure and generally referenced by numeral 10. While the following description will be directed towards electrosurgical pencils it is envisioned that the features and concepts (or portions thereof) of the present disclosure can be applied to any electrosurgical type instrument, e.g., forceps, suction coagulator, vessel sealers, etc.

Figure 2:
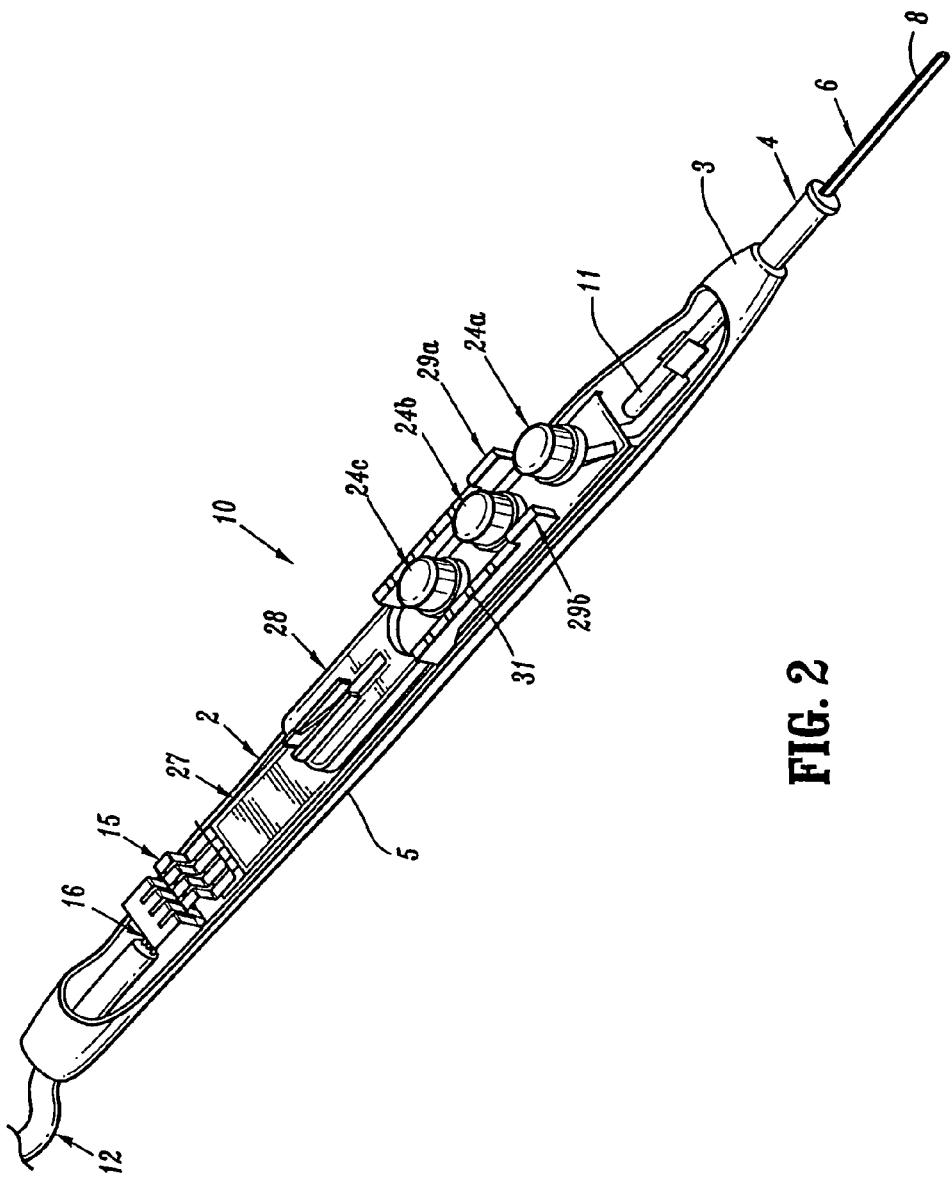
FIG. 2 is a partially broken away perspective view of the electrosurgical pencil of FIG. 1.
Figure 3:
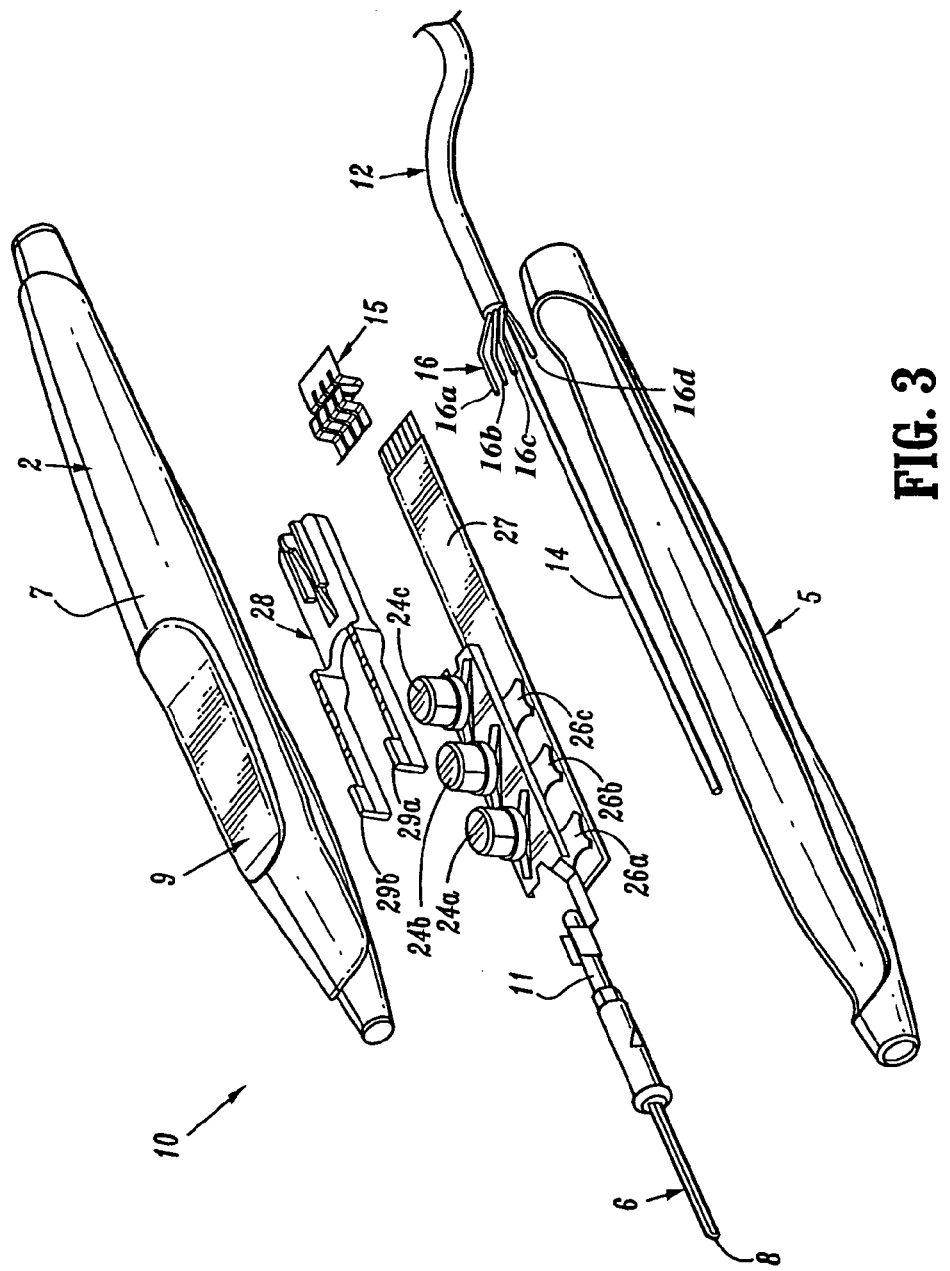
FIG. 3 is an exploded perspective view of the electrosurgical pencil of FIGS. 1 and 2.
Figure 4:
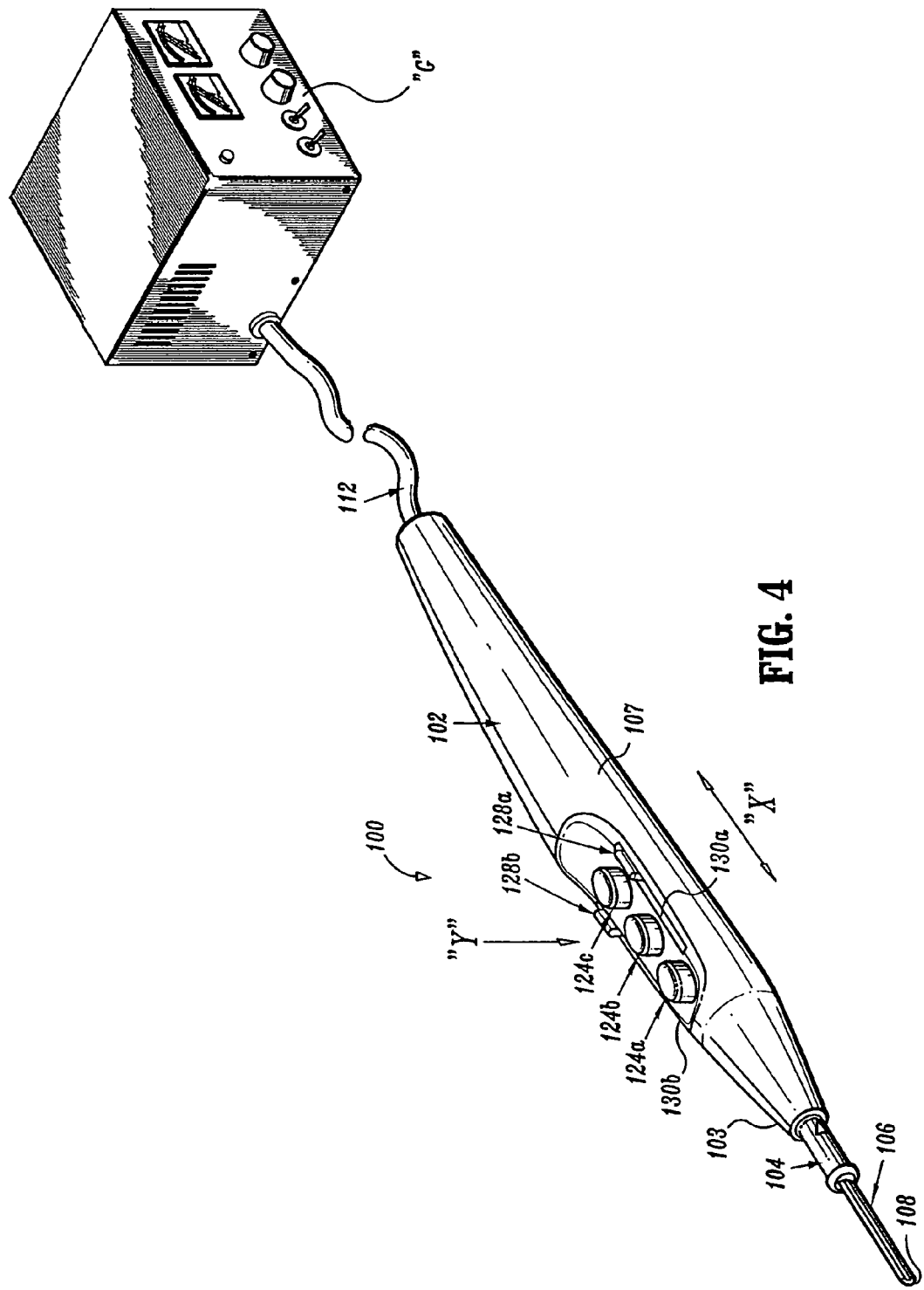
FIG. 4 is a perspective view of an electrosurgical pencil in accordance with another embodiment of the present disclosure.

As seen in FIGS. 1–3, electrosurgical pencil 10 includes an elongated housing 2 configured and adapted to support a blade receptacle 4 at a distal end 3 thereof which, in turn, receives a replaceable electrocautery end effector 6 in the form of a loop and/or blade therein. Electrocautery blade 6 is understood to include a planar blade, a loop, a needle and the like. A distal end portion 8 of blade 6 extends distally from receptacle 4 while a proximal end portion 11 (see FIG. 3) of blade 6 is retained within distal end 3 of housing 2. It is contemplated that electrocautery blade 6 is fabricated from a conductive type material, such as, for example, stainless steel, or is coated with an electrically conductive material.

As shown, electrosurgical pencil 10 is coupled to a conventional electrosurgical generator "G" via a cable 12. Cable 12 includes a transmission wire 14 (see FIG. 3) which electrically interconnects electrosurgical generator "G" with proximal end portion 11 of electrocautery blade 6. Cable 12 further includes control wires 16 which electrically interconnect mode activation switches (as will be described in greater detail below), supported on an outer surface 7 of housing 2, with electrosurgical generator "G". For the purposes herein the terms "switch" or "switches" includes electrical actuators, mechanical actuators, electromechanical actuators (rotatable actuators, pivotable actuators, toggle-like actuators, buttons, etc.) or optical actuators.

Turning back to FIGS. 1–3, as mentioned above, electrosurgical pencil 10 further includes at least one activation switch, preferably three activation switches 24a–24c, each of which are supported on an outer surface 7 of housing 2. Each activation switch 24a–24c is operatively connected to a location on a tactile element 26a–26c (e.g., a snap-dome is shown) which, in turn, controls the transmission of RF electrical energy supplied from generator "G" to electrosurgical blade 6. More particularly, tactile elements 26a–26c are operatively connected to a voltage divider network 27 (hereinafter "VDN 27") which forms a switch closure (e.g., here shown as a film-type potentiometer). For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series which are provided with taps at certain points to make available a fixed or variable fraction of the applied voltage.

In use, depending on which activation switch 24a–24c is depressed a respective switch 26a–26c is pressed into contact with VDN 27 and a characteristic signal is transmitted to electrosurgical generator "G" via control wires 16. Control wires 16a–16c are preferably electrically connected to switches 26a–26c via a terminal 15 (see FIGS. 2 and 3) operatively connected to VDN 27. By way of example only, electrosurgical generator "G" may be used in conjunction with the device wherein generator "G" includes a circuit for interpreting and responding to the VDN settings.

Activation switches 24a–24c are configured and adapted to control the mode and/or "waveform duty cycle" to achieve a desired surgical intent. For example, first activation switch 24a can be set to deliver a characteristic signal to electrosurgical generator "G" which in turn transmits a duty cycle and/or waveform shape which produces a cutting and/or dissecting effect/function. Meanwhile, second activation switch 24b can be set to deliver a characteristic signal to electrosurgical generator "G" which in turn transmits a duty cycle and/or waveform shape which produces a blending effect/function (e.g., a combination of a dissecting and a hemostatic effect/function). Finally, third activation switch 24c can be set to deliver a characteristic signal to electrosurgical generator "G" which in turn transmits a duty cycle and/or waveform shape which produces a hemostatic effect/function.

Fourth control wire 16d (i.e., a return control wire) is preferably connected to proximal end 11 of electrocautery blade 6. This prevents electrosurgical current, induced in control wires 16a–16c, from flowing through activation switches 24a–24c to electrocautery blade 6. This in turn, increases the longevity and life of switches 24a–24c.

As such, switches 24a–24c may be selected which are less complex and/or which are relatively inexpensive since the switch does not have to transmit current during activation. For example, if fourth control wire 16d is provided, switches 24a–24b may be constructed by printing conductive ink on a plastic film. On the other hand, if a fourth control wire 16d is not provided, switches may be of the type made of standard stamped metal which add to the overall complexity and cost of the instrument.

Figure 16:
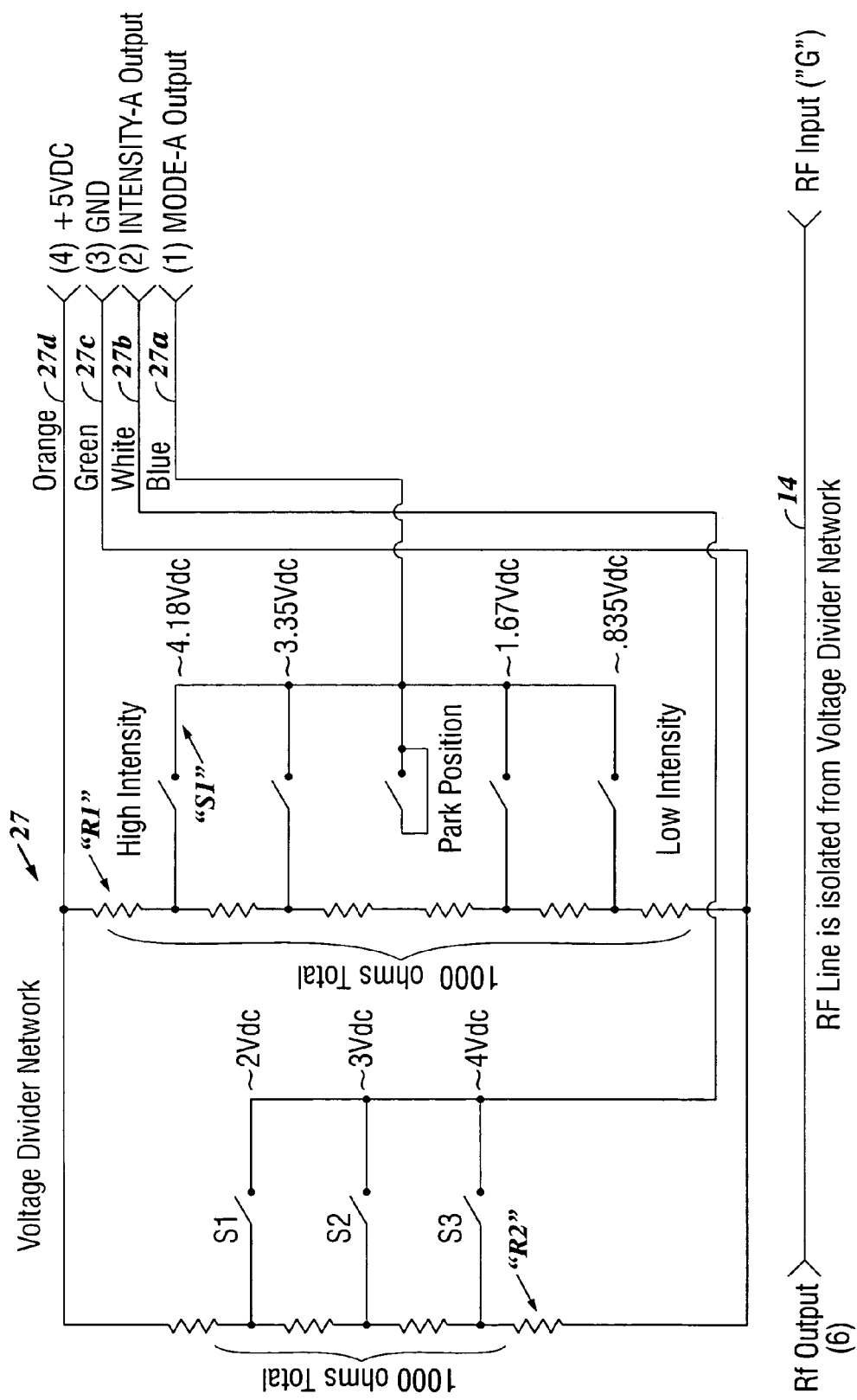
FIG. 16 is a schematic illustration of the voltage divider network of the present disclosure.

With reference to FIG. 16, in accordance with an embodiment of the present disclosure, a voltage divider network (VDN) 27, for inter-connecting control wires 16a–16d to activation and electrosurgical switches 24a–24c and electrocautery power wire 14 to blade 6, is shown. VDN 27 includes a first transmission line 27a, electrically connected to one of control wires 16a–16d, for example control wire 16a, to operate the various modes of electrosurgical pencil 10. VDN 27 includes a second transmission line 27b, electrically connected to one of control wires 16a–16d, for example control wire 16b, to operate the various intensities of electrosurgical pencil 10. VDN 27 includes a third and fourth transmission line 27c and 27d, respectively, to apply a voltage across VDN 27. For example, third transmission line 27c may be isolated or grounded and transmission line 27d may transmit +5 volts.

By way of example only, VDN 27 may include a plurality of resistors "R1" (e.g., 6 resistors), connected in a first series between transmission line 27c and transmission line 27d. Preferably, resistors "R1" combine to total about 1000 ohms of resistance. The first series of resistors "R1" are substantially each separated by a first set of switches "S1". Preferably, each switch of the first set of switches "S1" is electrically connected between adjacent resistors "R1" and transmission line 27a of VDN 27. In operation, depending on which switch or switches of the first set of switches "S1" is/are closed, a different mode of operation for electrosurgical pencil 10 is activated.

Additionally, by way of example only, VDN 27 may include a plurality of resistors "R2" (e.g., 4 resistors), connected in a second series between transmission line 27c and transmission line 27d. Preferably, resistors "R2" combine to total about 1000 ohms of resistance. The second series of resistors "R2" are each separated by a second set of switches "S2". Preferably, each switch of the second set of switches "S2" is electrically connected between adjacent resistors "R2" and transmission line 27b of VDN 27. In operation, depending on which switch or switches of the second set of switches "S2" is/are closed, a different intensity of RF energy is transmitted by electrosurgical pencil 10.

Also as depicted in FIG. 16, transmission wire 14 is isolated from or otherwise completely separate from VDN 27. In particular, transmission wire 14 extends directly from the RF input or generator "G" to the RF output or to electrocautery blade 6.

The hemostatic effect/function can be defined as having waveforms with a duty cycle from about 1% to about 12%. The blending effect/function can be defined as having waveforms with a duty cycle from about 12% to about 75%. The cutting and/or dissecting effect/function can be defined as having waveforms with a duty cycle from about 75% to about 100%. It is important to note that these percentages are approximated and may be customized to deliver the desired surgical effect for various tissue types and characteristics.

Electrosurgical pencil 10 further includes an intensity controller 28 slidingly supported on housing 2. Intensity controller 28 includes a pair of nubs 29a, 29b which are slidingly supported, one each, in respective guide channels 30a, 30b, formed in outer surface 7 of housing 2 on either side of activations switches 24a–24c. By providing nubs 29a, 29b on either side of activation switches 24a–24c, controller 28 can be easily manipulated by either hand of the user or the same electrosurgical pencil can be operated by a right-handed or a left-handed user.

Preferably, intensity controller 28 is a slide potentiometer wherein nubs 29a, 29b have a first position (e.g., proximal-most position closest to cable 12) corresponding to a relative low intensity setting, a second position (e.g., a distal-most position closest to electrocautery end effector 6) corresponding to a relative high intensity setting, and a plurality of intermediate positions corresponding to intermediate intensity settings. As can be appreciated, the intensity settings from proximal end to distal end may be reversed as well, e.g., high to low. It is contemplated that nubs 29a, 29b of intensity controller 28 and corresponding guide channels 30a, 30b may be provided with a series of cooperating discreet or dented positions defining a series of positions, preferably five, to allow easy selection of the output intensity from the low intensity setting to the high intensity setting. The series of cooperating discreet or detented positions also provide the surgeon with a degree of tactile feedback. As best seen in FIG. 2, intensity controller 28 can include a series of indicia 31 provided thereon which are visible through guide channels 30a, 30b. Indicia 31 are preferably a series of numbers (e.g., numbers 1–5) which reflect the level of intensity that is to be transmitted. Alternatively, level indicators may be printed alongside the sides of guide channels 30a, 30b along which nubs 29a, 29b slide.

Intensity controller 28 is configured and adapted to adjust the power parameters (e.g., voltage, power and/or current intensity) and/or the power verses impedance curve shape to affect the perceived output intensity. For example, the greater intensity controller 28 is displaced in a distal direction the greater the level of the power parameters transmitted to electrocautery blade 6. Conceivably, current intensities can range from about 60 mA to about 240 mA when using an electrosurgical blade and having a typical tissue impedance of about 2K ohms. An intensity level of 60 mA provides very light and/or minimal cutting/dissecting/hemostatic effects. An intensity level of 240 mA provides very aggressive cutting/dissecting/hemostatic effects. Accordingly, the preferred range of current intensity is from about 100 mA to about 200 mA at 2K ohms.

The intensity settings are preferably preset and selected from a look-up table based on a choice of electrosurgical instruments/attachments, desired surgical effect, surgical specialty and/or surgeon preference. The selection may be made automatically or selected manually by the user. The intensity values may be predetermined or adjusted by the user.

In operation and depending on the particular electrosurgical function desired, the surgeon depresses one of activation switches 24a–24c, in the direction indicated by arrow "Y" (see FIG. 1) thereby urging a corresponding switch 26a–26c against VDN 27 and thereby transmitting a respective characteristic signal to electrosurgical generator "G". For example, the surgeon can depress activation switch 24a to perform a cutting and/or dissecting function, activation switch 24b to perform a blending function, or activation switch 24c to perform a hemostatic function. In turn, generator "G" transmits an appropriate waveform output to electrocautery blade 6 via transmission wire 14.

In order to vary the intensity of the power parameters of electrosurgical pencil 10, the surgeon displaces intensity controller 28 in the direction indicated by double-headed arrow "X". As mentioned above, the intensity can be varied from approximately 60 mA for a light effect to approximately 240 mA for a more aggressive effect. For example, by positioning nubs 29a, 29b of intensity controller 28 closer to the proximal-most end of guide channels 30a, 30b (i.e., closer to cable 12) a lower intensity level is produced and by positioning nubs 29a, 29b of intensity controller 28 closer to the distal-most end of guide channels 30a, 30b (i.e., closer to electrocautery end effector 6) a larger intensity level is produced resulting in a more aggressive effect being produced. It is envisioned that when nubs 29a, 29b of intensity controller 28 are positioned at the proximal-most end of guide channels 30a, 30b, VDN 27 is set to a null and/or open position. Preferably, electrosurgical pencil 10 is shipped with intensity controller 28 set to the null and/or open positions.

Preferably, intensity controller 28 controls the intensity level of the electrosurgical energy transmitted by all three activation switches 24a–24c, simultaneously. In other words, as nubs 29a, 29b of intensity controller 28 are positioned relative to guide channels 30a, 30b, the intensity level of the electrosurgical energy transmitted to all three activation switches 24a–24c is set to the same value of slide potentiometer or intensity controller 28.

As a safety precaution, it is envisioned that when electrosurgical pencil 10 is changed from one mode to another, intensity controller 28 may be configured such that it must be reset (i.e., nubs 29a, 29b, re-positioned to the proximal-most end of guide channels 30a, 30b thus setting VDN 27 to the null and/or open position). After being reset, intensity controller 28 may be adjusted as needed to the desired and/or necessary intensity level for the mode selected.

It is envisioned and contemplated that VDN 27 may also include an algorithm which stores the last intensity level setting for each mode. In this manner, intensity controller 28 does not have to be reset to the last operative value when the particular mode is re-selected.

The combination of placing VDN 27 and fourth control wire 16d in electrosurgical pencil 10 essentially places the entire resistor network of the electrosurgical system (e.g., electrosurgical pencil 10 and the source of electrosurgical energy "G") within electrosurgical pencil 10. Conventional electrosurgical systems typically include a current limiting resistor disposed within the electrosurgical pencil, for activating the electrosurgical pencil, and a second resistor network disposed in the source of electrosurgical energy, for controlling the intensity of the electrosurgical energy transmitted. In accordance with the present disclosure, both the first and the second resistor networks are disposed within electrosurgical pencil 10, namely, the first resistor network as evidenced by activation switches 24a–24c, and the second resistor network as evidenced by intensity controller 28.

As described above, intensity controller 28 can be configured and adapted to provide a degree of tactile feedback. Alternatively, audible feedback can be produced from intensity controller 28 (e.g., a "click"), from electrosurgical energy source "G" (e.g., a "tone") and/or from an auxiliary sound-producing device such as a buzzer (not shown).

Preferably, as seen in FIGS. 1 and 3, intensity controller 28 and activation switches 24a–24c are supported in a recess 9 formed in outer wall 7 of housing 2. Desirably, activation switches 24a–24c are positioned at a location where the fingers of the surgeon would normally rest when electrosurgical pencil 10 is held in the hand of the surgeon while nubs 29a, 29b of intensity controller 28 are placed at locations which would not be confused with activation switches 24a–24c. Alternatively, nubs 29a, 29b of intensity controller 28 are positioned at locations where the fingers of the surgeon would normally rest when electrosurgical pencil 10 is held in the hand of the surgeon while activation switches 24a–24c are placed at locations which would not be confused with nubs 29a, 29b of intensity controller 28. In addition, recess 9 formed in outer wall 7 of housing 2 advantageously minimizes inadvertent activation (e.g., depressing, sliding and/or manipulating) of activation switches 24a–24c and intensity controller 28 while in the surgical field and/or during the surgical procedure.

As seen in FIG. 3, electrosurgical pencil 10 includes a molded/contoured hand grip 5 which substantially surrounds the distal and proximal ends of housing 2 as well as the underside of housing 2. Contoured hand grip 5 is shaped and dimensioned to improve the handling of electrosurgical pencil 10 by the surgeon. Accordingly, less pressure and gripping force is required to use and/or operate electrosurgical pencil 10 thereby potentially reducing the fatigue experienced by the surgeon and to prevent movement of electrosurgical pencil 10 during proximal and distal adjustments of nubs 29a and 29b.

Turning now to FIGS. 4–8, an electrosurgical pencil constructed in accordance with another embodiment of the present disclosure is shown generally as 100. Electrosurgical pencil 100 includes at least one activation switch, preferably three activation switches 124a–124c, each of which are supported on an outer surface 107 of housing 102. Each activation switch 124a–124c is operatively connected to a respective switch 126a–126c which, in turn, controls the transmission of RF electrical energy supplied from generator "G" to electrosurgical blade 106. More particularly, switches 126a–126c are electrically coupled to control loop 116 and are configured to close and/or complete control loop 116 to thereby permit RF energy to be transmitted to electrocautery blade 106 from electrosurgical generator "G".

Activation switches 124a–124c are configured and adapted to control the mode and/or "waveform duty cycle" to achieve a desired surgical intent in the same manner as activation switches 24a–24c of electrosurgical pencil 10 described above.

Electrosurgical pencil 100 further includes at least one intensity controller, preferably two intensity controllers 128a and 128b, each of which are slidingly supported in guide channels 130a, 130b, respectively, which are formed in outer surface 107 of housing 102. Preferably, each intensity controller 128a and 128b is a slide-like potentiometer. It is contemplated that each intensity controller 128a and 128b and respective guide channel 130a and 130b may be provided with a series of cooperating discreet or detented positions defining a series of positions, preferably five, to allow easy selection of output intensity from a minimum amount to a maximum amount. The series of cooperating discreet or detented positions also provide the surgeon with a degree of tactile feedback. It is further envisioned that one of the series of positions for intensity controllers 128a, 128b is an off position (i.e., no level of electrical or RF energy is being transmitted).

Intensity controllers 128a, 128b is configured and adapted to adjust one of the power parameters (e.g., voltage, power and/or current intensity) and/or the power verses impedance curve shape to affect the perceived output intensity.

For example, the greater intensity controllers 128a, 128b are displaced in a distal direction (i.e., in the direction of electrocautery blade 106) the greater the level of the power parameters transmitted to electrocautery blade 106. Conceivably, current intensities can range from about 60 mA to about 240 mA when using an electrosurgical blade and having a typical tissue impedance of about 2000 ohms. An intensity level of 60 mA provides very light and/or minimal cutting/dissecting/hemostatic effects. An intensity level of 240 mA provides very aggressive cutting/dissecting/hemostatic effects. Accordingly, the preferred range of current intensity is from about 100 mA to about 200 mA at 2K ohms.

The intensity settings are preferably preset and selected from a look-up table based on a choice of electrosurgical instruments/attachments, desired surgical effect, surgical specialty and/or surgeon preference. The selection may be made automatically or selected manually by the user. The intensity values may be predetermined or adjusted by the user.

In operation and depending on the particular electrosurgical function desired, the surgeon depresses one of activation switches 124a–124c, in the direction indicated by arrow "Y" (see FIGS. 4 and 7) thereby closing a corresponding switch 126a–126c and closing and/or completing control loop 116. For example, the surgeon can depress activation switch 124a to perform a cutting or dissecting function, activation switch 124b to perform a dissecting/hemostatic function, or activation switch 124c to perform a hemostatic function. In turn, generator "G" transmits an appropriate waveform output to electrocautery blade 106 via transmission wire 114.

In order to vary the intensity of the power parameters of electrosurgical pencil 100, preferably, the current intensity, the surgeon displaces at least one of intensity controllers 128a, 128b in the direction indicated by double-headed arrow "X". As mentioned above, the intensity can be varied from approximately 60 mA for a light effect to approximately 240 mA for a more aggressive effect. For example, by positioning one of intensity controllers 128a, 128b closer to the proximal-most end (i.e., closer to cable 112) a light effect is produced and by positioning one of intensity controllers 128a, 128b closer to the distal-most end (i.e., closer to electrocautery blade 106) a more aggressive effect is produced. As described above, each intensity controller 128a, 128b can be configured and adapted to provide a degree of tactile feedback. Alternatively, audible feedback can be produced from each intensity controller 128a, 128b (e.g., a "click"), electrosurgical energy source "G" (e.g., a "tone") and/or an auxiliary sound-producing device such as a buzzer (not shown).

In an alternative embodiment, as seen in FIGS. 9 and 10, sliding intensity controllers 128a, 128b have been replaced with intensity controllers 228a, 228b in the form of dial-like VDNs. Intensity controllers 228a, 228b function to vary the intensity of the power parameters via a rotation of dial controllers 228a, 228b in either a clockwise or counter-clockwise direction as indicated by double headed arrow "Z". As seen in FIGS. 6 and 7, dial controllers 228a, 228b are disposed externally of housing 102, however, it is contemplated that dial controllers 228a, 228b are disposed within housing 102 with only a portion projecting therefrom for manipulation by the surgeon. It is envisioned that intensity controllers 228a, 228b can be a single controller having a pair of opposed knobs/dials provided, one each, on either side of housing 102. In this manner, the intensity can be controlled from either side of electrosurgical pencil 100.

Since the surgeon has a number of controls at his finger tips, the surgeon is able to create a pallet of varying therapeutic effects ranging from a pure "cutting" effect to a pure "coagulating" effect and a number of effects in between at a number of intensities. Moreover, with some pre-setting of the electrosurgical energy source "G", electrosurgical pencil 100 will have all the useful settings available to the surgeon within the sterile field. Accordingly, it is not necessary that the surgeon interact with hardware outside the sterile field (e.g., electrosurgical energy source "G") once the surgical procedure begins thus allowing the surgeon to focus attention on the surgical procedure.

While embodiments of electrosurgical pencils according to the present disclosure have been described herein, it is not intended that the disclosure be limited there and the above description should be construed as merely exemplifications of preferred embodiments. Those skilled in the art will envision other modifications within the scope and spirit of the present disclosure.

Figure 11:
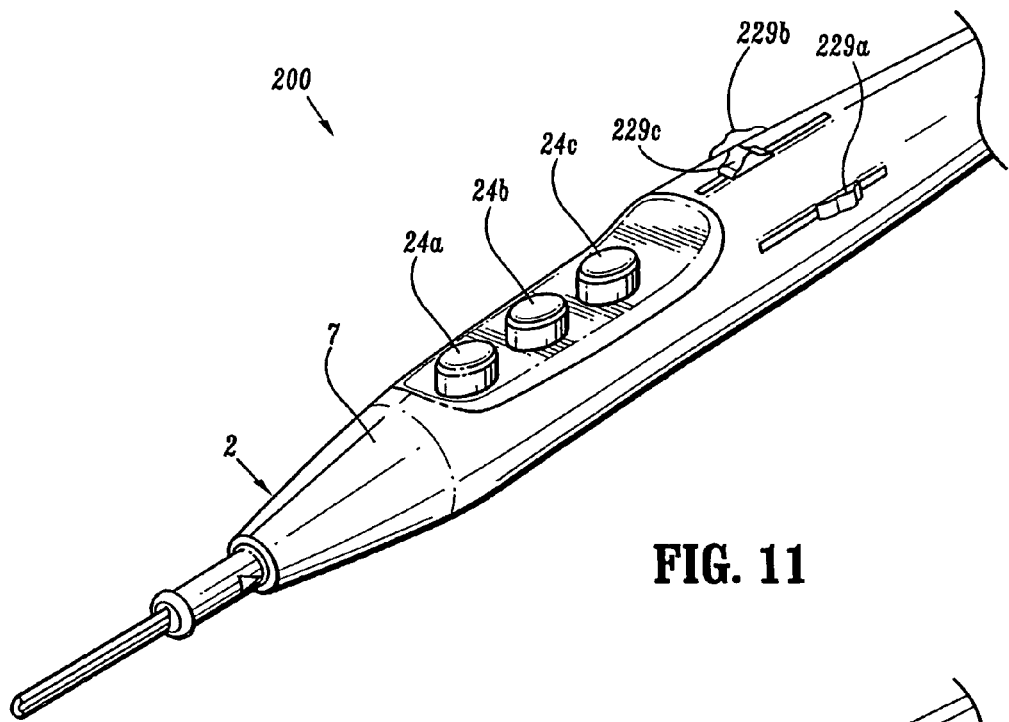
FIG. 11 is a front perspective view of a distal end portion of an electrosurgical pencil according to yet another embodiment of the present disclosure.

For example, as seen in FIG. 11, an alternative embodiment of an electrosurgical pencil is shown generally as 200. Electrosurgical pencil 200 is similar to electrosurgical pencil 10 and/or 100 and will only be discussed in detail to the extent necessary to identify differences in construction and operation. As seen in FIG. 11, electrosurgical pencil 200 includes a plurality of nubs, preferably, three nubs, 229a–229c which are slidingly supported, one each, in respective guide channels 230a–230c, formed in outer surface 7 of housing 2, at a position proximal of activation switches 24a–24c. Each nub 229a–229c is operatively engaged with a slide potentiometer.

Accordingly, electrosurgical pencil 200 can be configured such that each activation switch 24a–24c is a separate mode, such as, for example, activation switch 24a can be set such that electrosurgical pencil 200 performs "division" when depressed, activation switch 24b can be set such that electrosurgical pencil 200 performs "division with hemostasis" when depressed, and activation switch 24c can be set such that electrosurgical pencil 200 performs "hemostasis" when depressed. In addition, each nub 229a–229c is in operative engagement with a corresponding activation switch 24a–24c such that the power for each mode of operation of electrosurgical pencil 200 can be independently adjusted.

Figure 12:
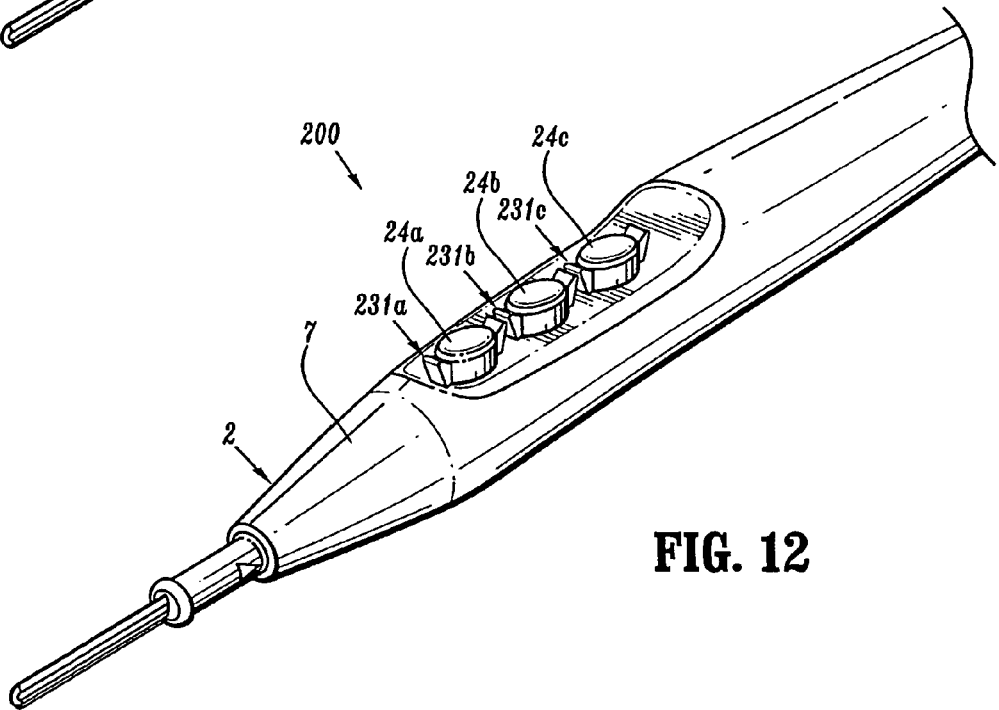
FIG. 12 is a front perspective view of a distal end portion of an electrosurgical pencil according to still another embodiment of the present disclosure.

As seen in FIG. 12, nubs 229a–229c of electrosurgical pencil 200 have been replaced with toggles 231a–231c operatively engaged with a respective activation switch 24a–24c. Each toggle 231a–231c can be operatively engaged with a rocker-type switch (not shown) or a rotational dial (not shown) in place of the slide-type potentiometer described above.

Figure 13:
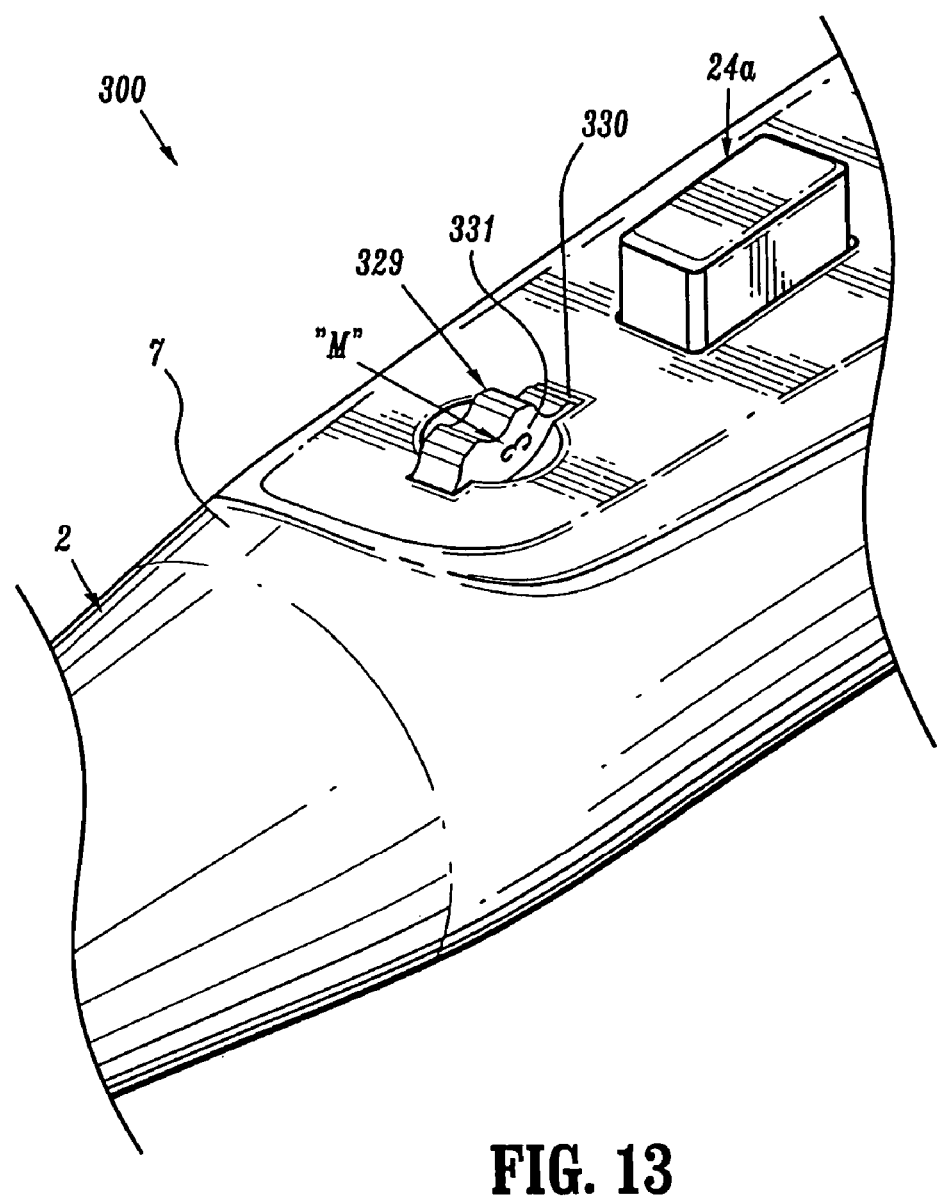
FIG. 13 is an enlarged perspective view of a portion of an electrosurgical pencil illustrating a set of exemplary switches disposed thereon.
Figure 14:
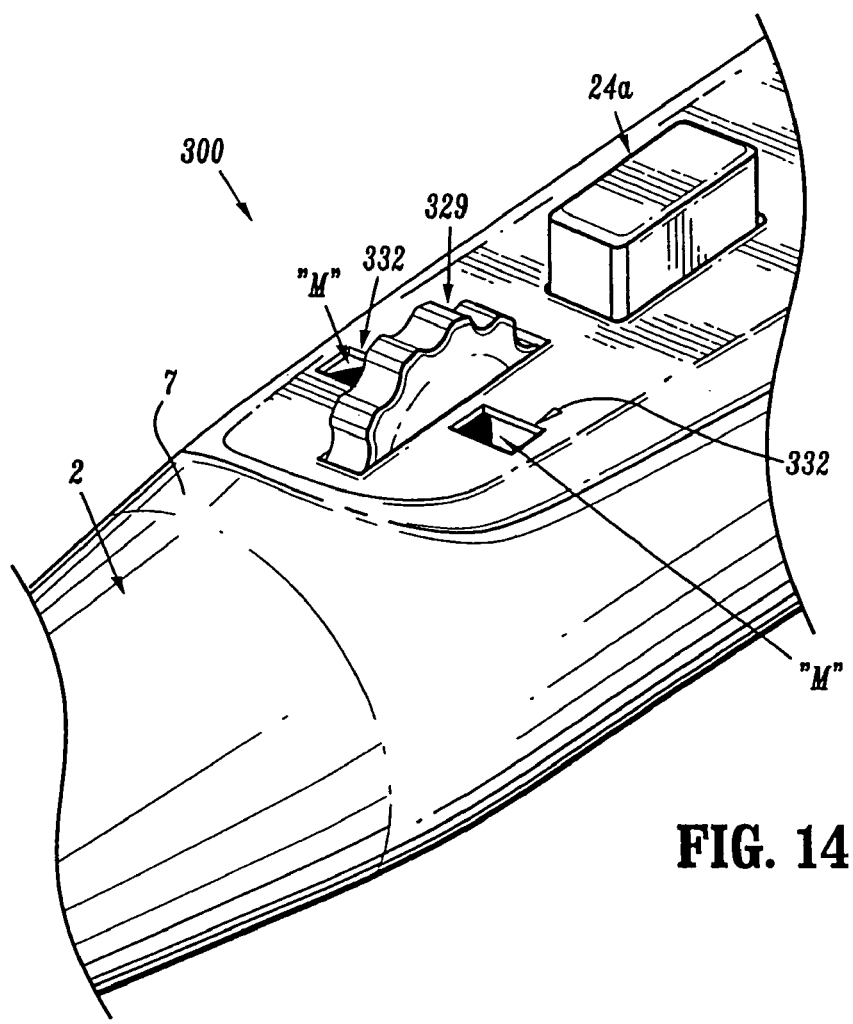
FIG. 14 is an enlarged perspective view of a portion of an electrosurgical pencil illustrating another set of exemplary switches disposed thereon.
Figure 15:
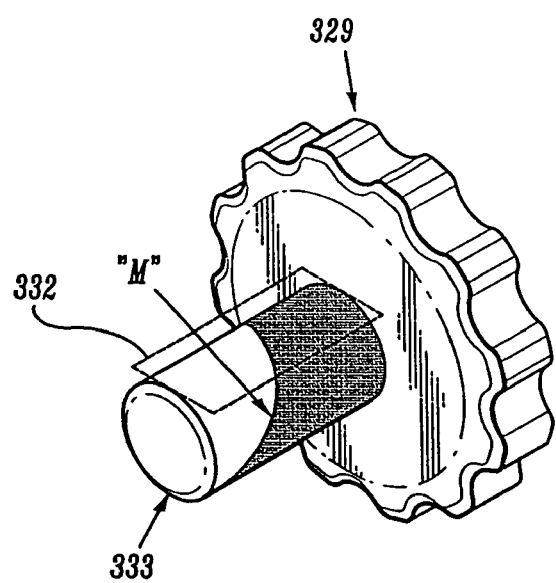
FIG. 15 is a perspective view of the switch of FIG. 14.

Turning now to FIGS. 13–15, an electrosurgical pencil, in accordance with still another embodiment of the present disclosure, is generally designated as 300. Electrosurgical pencil 300 is similar to electrosurgical pencil 10 and/or 100 and will only be discussed in detail to the extent necessary to identify differences in construction and operation. As seen in FIGS. 13 and 14, nubs 29a, 29b have been replaced with a dial 329 rotatably supported in an aperture 330 formed in outer surface 7 of housing 2. Preferably, dial 329 is positioned forward of activation switch 24a such that dial 329 is not inadvertently rotated during the depression of any one of activation switches 24a–24c.

As seen in FIG. 13, a side surface 331 of dial 329 can be provided with indicia and/or markings "M" in the form of a scale and/or other form of gradient to indicate to the surgeon the degree of and/or level of power at which electrosurgical pencil 300 is set.

As seen in FIGS. 14 and 15, windows 332 can be formed on either side of dial 329 in outer surface 7 of housing 2. As seen in FIG. 15, windows 332 provide the surgeon with visibility to indicia "M" provided on stub 333 extending from the central axis of dial 329. Indicia "M" can be in the form of numbers, letters, colors and, as seen in FIGS. 14 and 15, an enlarging gradient. It is envisioned that each dial 329 can perform a dual function, for example, dial 329 can be rotated to set the desired power level and can be pressed down to activate the electrosurgical pencil with the desired mode.

Figure 17:
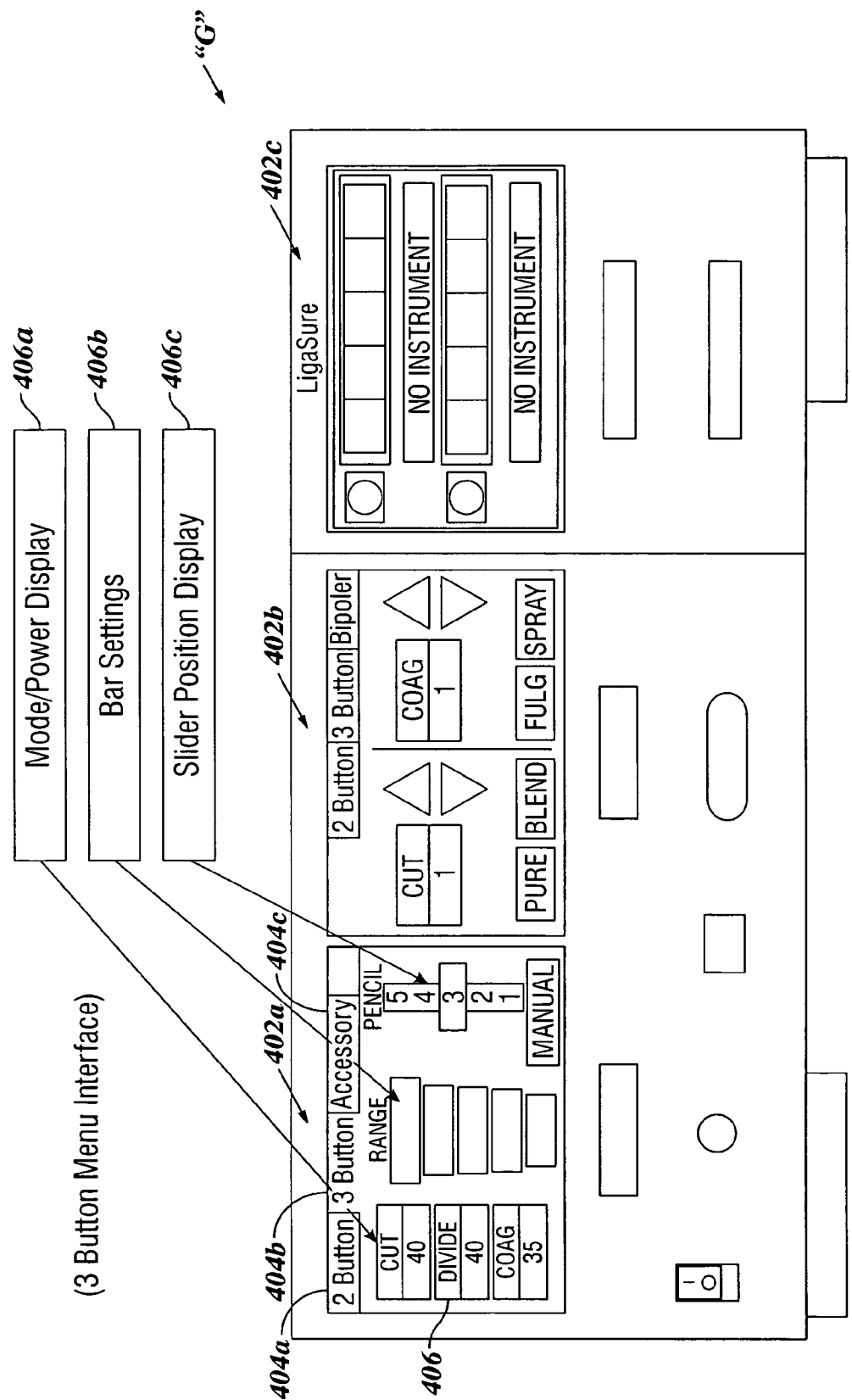
FIG. 17 is a front elevational view of an electrosurgical generator of the present disclosure.

Turning now to FIG. 17, an electrosurgical generator in accordance with an embodiment of the present disclosure, is shown generally as "G". Electrosurgical generator "G" includes a plurality of displays 402, here shown with three displays, 402a–402c. Each of displays 402a–402c may include a number of screens, windows or tabs as depicted by numerals 404a–404c.

Each screen 404a–404c of each display 402a–402c may include a number of display elements 406. By way of example only, as seen in FIG. 17, screen 404b of display 402a includes at least three display elements 406a–406c. Display element 406a may show the mode and power setting of electrosurgical generator "G" to be transmitted to electrosurgical pencil 10. Display element 406b may show a range or bar setting of electrosurgical generator "G" to be transmitted to electrosurgical pencil 10. Display element 406c may show the position of the slider on electrosurgical pencil 10.

Turning now to FIGS. 18–22, a flow chart (FIG. 18) depicting a method of using electrosurgical pencil 10 with electrosurgical generator "G" of FIG. 17, for a plurality of settings (FIGS. 19–22), is shown and will be described. Initially, the bar level or setting of electrosurgical generator "G" is selected by the user. By way of example only, as seen in FIGS. 17, 19 and 20, electrosurgical generator "G" includes five (5) levels or settings, although other numbers of levels or settings are possible. By selecting a particular bar level or setting, electrosurgical generator "G" is set to deliver power and current, for each mode of operation, at predetermined levels, as seen in the tables of FIGS. 19 and 20.

Figure 18:
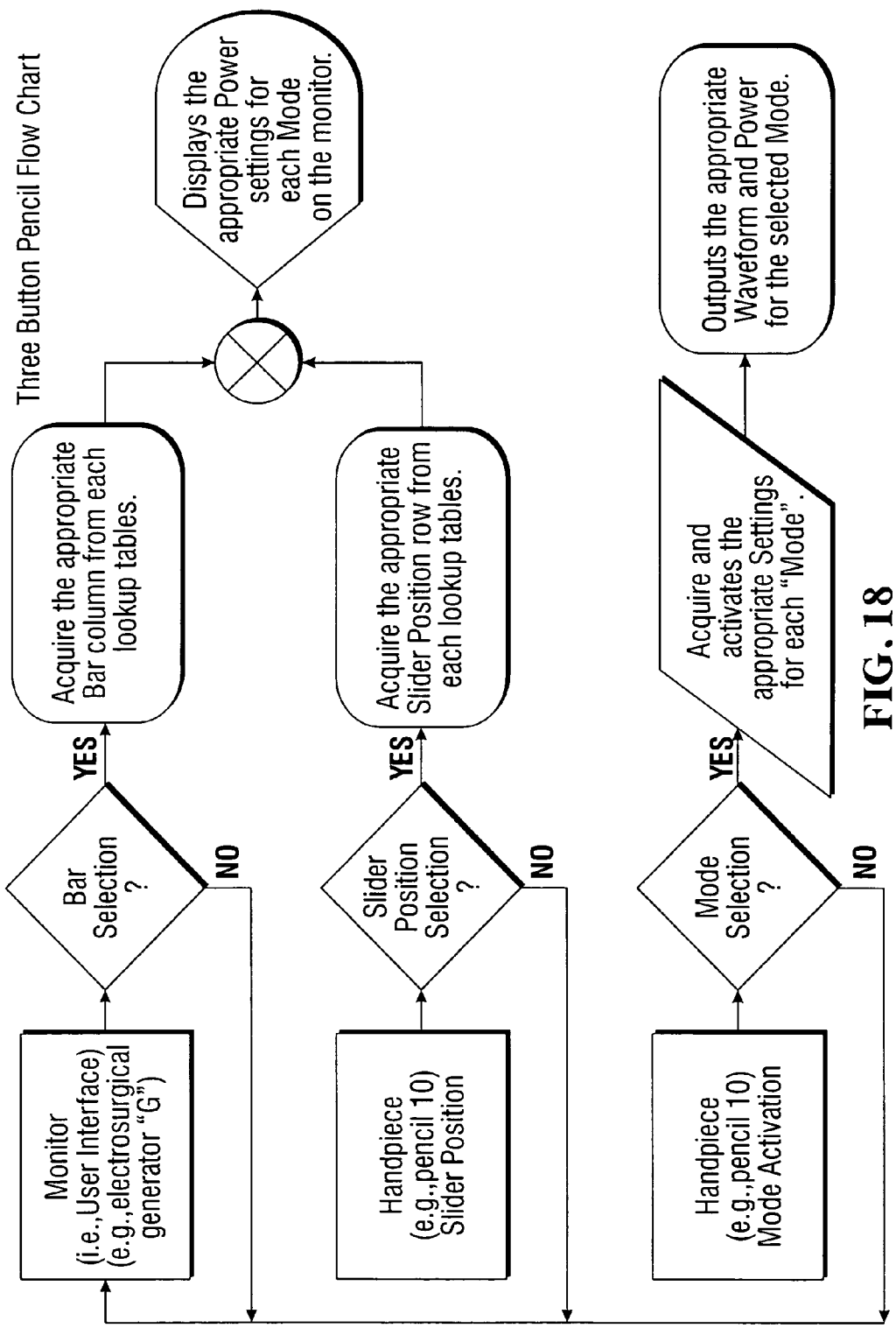
FIG. 18 is a flow chart of a mode of operation of the electrosurgical pencil of FIGS. 1–3.

With the bar level or setting selected, as needed or desired, as seen in FIG. 18, the user sets intensity controller 28 (FIG. 2) by sliding nub 29a and/or 29b to one of a number of positions along guide channels 30a, 30b of electrosurgical pencil 10. While nubs 29a, 29b of intensity controller 28 are shown and described as being settable to five (5) positions along electrosurgical pencil 10, it is envisioned and within the scope of the present disclosure that electrosurgical pencil 10 may be configured to provide more or fewer than five (5) settable positions for nubs 29a, 29b of intensity controller 28. By positioning intensity controller 28 to a particular setting, electrosurgical generator "G" is set to deliver power and current for each mode of operation, at a predetermined level, as seen in the tables of FIGS. 19 and 20.

With the bar level or setting selected and intensity controller 28 set, as seen in FIG. 18, the necessary or desired mode of operation of electrosurgical pencil 10 is activated by depressing the appropriate or corresponding activation switch 24a–24c (FIG. 1). As described above, if switch 24a is depressed, then the cut mode is activated, if switch 24b is depressed, then the blend or dividing mode is activated, and if switch 24c is depressed, then the coagulating mode is activated.

For example, as seen in FIG. 19, if the bar level or setting of electrosurgical generator "G" is set to "2" and the position of intensity controller 28 is set to "4", then the power value for each mode of operation is as follows: 150 watts in Mode 1 for cutting; 100 watts in Mode 2 for blending or dividing; and 60 watts in Mode 3 for coagulating. Additionally, the electrical current value for this particular setting, as seen in FIG. 20, is as follows: 0.625 amps in Mode 1 for cutting; 0.500 amps in Mode 2 for blending or dividing; and 0.500 amps in Mode 3 for coagulating.

As seen in FIG. 21, the output frequency and duty cycle for each mode of operation is shown. Also shown in FIG. 21 is a summary of the various electrical current settings, from FIG. 20, for each mode of operation, for each position of intensity controller 28 of electrical pencil 10, when the bar or level setting for electrosurgical generator "G" is set to "2".

In FIG. 22, a summary of the various power settings, from FIG. 19, for each mode of operation, for each position of intensity controller 28 of electrical pencil 10, when the bar or level setting for electrosurgical generator "G" is set to "2", is shown.

It is further envisioned that any of the electrosurgical pencils disclosed herein can be provided with a lock-out mechanism/system (not shown) wherein when one of the activation switches is depressed, the other remaining activation switches can either not be depressed or can not cause transmission of electrosurgical energy to electrocautery blade 106.

It is also envisioned that the electrosurgical pencil 100 may include a smart recognition technology which communicates with the generator to identify the electrosurgical pencil and communicate various surgical parameters which relate to treating tissue with electrosurgical pencil 100. For example, the electrosurgical pencil 100 may be equipped with a bar code or Aztec code which is readable by the generator and which presets the generator to default parameters associated with treating tissue with electrosurgical pencils. The bar code or Aztec code may also include programmable data which is readable by the generator and which programs the generator to specific electrical parameters prior to use.

Other smart recognition technology is also envisioned which enable the generator to determine the type of instrument being utilized or to insure proper attachment of the instrument to the generator as a safety mechanism. One such safety connector is identified in U.S. patent application Ser. No. 10/718,114, filed Nov. 20, 2003, the entire contents of which being incorporated by reference herein. For example, in addition to the smart recognition technology described above, such a safety connector can include a plug or male portion operatively associated with the electrosurgical pencil and a complementary socket or female portion operatively associated with the electrosurgical generator. Socket portion is "backward compatible" to receive connector portions of electrosurgical pencils disclosed therein and to receive connector portions of prior art electrosurgical instruments.

It is also envisioned that the current controls may be based on current density or designed to deliver a specific current for a defined surface area (amp/cm$^2$).

Although the subject apparatus has been described with respect to preferred embodiments, it will be readily apparent, to those having ordinary skill in the art to which it appertains, that changes and modifications may be made thereto without departing from the spirit or scope of the subject apparatus.

The invention claimed is:

1. An electrosurgical pencil, comprising:
    an elongated housing;
    an electrocautery electrode supported within the housing and extending distally from the housing, the electrocautery electrode being connected to a source of electrosurgical energy;
    a plurality of activation switches supported on the housing, each activation switch being configured and adapted to selectively complete a control loop extending from the source of electrosurgical energy upon actuation thereof; and
    at least one voltage divider network supported on the housing, the at least one voltage divider network being electrically connected to the source of electrosurgical energy for controlling the intensity of electrosurgical energy being delivered to the plurality of activation switches from the source of electrosurgical energy and for controlling the intensity of electrosurgical energy delivered to the plurality of activation switches returning from the electrocautery electrode, the at least one voltage divider network comprises at least one return control wire electrically inter-connecting the electrocautery electrode and the source of electrosurgical energy, the return control wire transmitting excess electrosurgical energy from the electrocautery electrode to the source of electrosurgical energy.

2. The electrosurgical pencil according to claim 1, wherein the at least one voltage divider network further comprises:
    a plurality of control wires electrically inter-connecting a respective activation switch to the source of electrosurgical energy, each control wire delivering electrosurgical energy from the source of electrosurgical energy to the electrocautery electrode.

3. The electrosurgical pencil according to claim 2, wherein the voltage divider network includes a slide potentiometer operatively associated with the housing.

4. The electrosurgical pencil according to claim 3, wherein the plurality of activation switches define a first resistor network disposed within the housing, and wherein the slide potentiometer defines a second resistor network disposed within the housing.

5. The electrosurgical pencil according to claim 4, wherein the slide potentiometer simultaneously controls the intensity of electrosurgical energy delivered to the plurality of activation switches.

6. The electrosurgical pencil according to claim 5, wherein the voltage divider network includes an algorithm which stores the last setting for each activation switch.

7. The electrosurgical pencil according to claim 6, wherein the voltage divider network includes an algorithm which requires the slide potentiometer to be set to zero each time the mode of operation of the electrosurgical pencil is changed.

8. The electrosurgical pencil according to claim 7, wherein the electrosurgical pencil includes three mode activation switches supported on the housing, wherein each of the three mode activation switches is configured and adapted to deliver a characteristic signal to a source of electrosurgical energy which source of electrosurgical energy in turn transmits a corresponding waveform duty cycle to the end effector.

9. The electrosurgical pencil according to claim 8, wherein a first mode activation switch activates a waveform duty cycle which produces a dissecting effect, a second mode activation switch activates a waveform duty cycle which produces a dissecting and hemostatic effect, and a third mode activation switch activates a waveform duty cycle which produces a hemostatic effect.

10. The electrosurgical pencil according to claim 9, wherein the at least one voltage divider network includes a pair of nubs slidably supported on the housing, one each, on either side of the activation switches.

11. The electrosurgical pencil according to claim 10, wherein the at least one voltage divider network has a first position corresponding to a minimum intensity, a second position corresponding to a maximum intensity and a plurality of positions between the first and second positions corresponding to intensities between the minimum and the maximum intensity.

12. The electrosurgical pencil according to claim 11, wherein the at least one voltage divider network is configured and adapted to vary a current intensity from a minimum of about 60 mA to a maximum of about 240 mA at 2K ohms.

13. The electrosurgical pencil according to claim 12, wherein the at least one voltage divider network is configured and adapted to vary a current intensity from a minimum of about 100 mA to a maximum of about 200 mA.

14. The electrosurgical pencil according to claim 13, wherein the at least one voltage divider network is set to the minimum when the at least one voltage divider network is placed at a proximal-most position and is set to the maximum when placed at a distal-most position.

15. The electrosurgical pencil according to claim 14, wherein the at least one voltage divider network is configured and adapted to provide a plurality of discreet intensity settings.

16. The electrosurgical pencil according to claim 14, wherein the at least one voltage divider network is configured and adapted to provide analog intensity settings.

17. The electrosurgical pencil according to claim 13, wherein the at least one voltage divider network is set to the minimum when the at least one voltage divider network is placed at a distal-most position and is set to the maximum when placed at a proximal-most position.

18. The electrosurgical pencil according to claim 13, wherein the waveform duty cycle of the activation switches varies with a change in intensity produced by the at least one voltage divider network.

19. The electrosurgical pencil according to claim 7, wherein at least one activation switch is configured and adapted to control a waveform duty cycle to achieve a desired surgical intent.

20. The electrosurgical pencil according to claim 19, further including a molded hand grip operatively supported on the housing.

21. The electrosurgical pencil according to claim 20, wherein the hand grip is shaped and dimensioned to reduce fatigue on the hand of the user.

22. The electrosurgical pencil according to claim 19, further including three mode activation switches supported on the housing.

23. The electrosurgical pencil according to claim 22, wherein each mode activation switch delivers a characteristic signal to the source of electrosurgical energy which in turn transmits a corresponding waveform duty cycle to the electrosurgical pencil.

24. The electrosurgical pencil according to claim 22, wherein a first activation switch delivers a first characteristic signal to the source of electrosurgical energy which in turn transmits a waveform duty cycle which produces a cutting effect, a second activation switch delivers a second characteristic signal to the source of electrosurgical energy which in turn transmits a waveform duty cycle which produces a blending effect, and wherein a third activation switch delivers a third characteristic signal to the source of electrosurgical energy which in turn transmits a waveform duty cycle which produces a coagulating effect.

25. The electrosurgical pencil according to claim 24, wherein the voltage divider network is a potentiometer.

26. The electrosurgical pencil according to claim 25, wherein the potentiometer is a rheostat having discreet values and configured and adapted to adjust the intensity of the waveform duty cycle corresponding to a particular activation switch.

27. The electrosurgical pencil according to claim 26, wherein the potentiometer has a plurality of intensity settings.

28. The electrosurgical pencil according to claim 27, wherein the potentiometer is configured and adapted to vary a current intensity from a minimum of about 60 mA to a maximum of about 240 mA at 2K ohms.

29. The electrosurgical pencil according to claim 27, wherein the potentiometer is configured and adapted to vary a current intensity from a minimum of about 100 mA to a maximum of about 200 mA at 2K ohms.

30. The electrosurgical pencil according to claim 29, wherein the potentiometer is slidably supported on the housing.

31. The electrosurgical pencil according to claim 30, wherein the potentiometer is set to a minimum when the potentiometer is placed at a first position and is set to a maximum when the potentiometer is placed at a second position.

32. The electrosurgical pencil according to claim 31, wherein the potentiometer is configured and adapted to provide a plurality of discreet intensity settings.

33. The electrosurgical pencil according to claim 32, wherein the electrocautery electrode is one of a blade, needle, a loop and a ball.

34. The electrosurgical pencil according to claim 32, wherein the slide potentiometer includes a pair of nubs slidably supported, one each, on either side of the plurality of activation switches such that the potentiometer is operable from either side of the electrosurgical pencil.

35. The electrosurgical pencil according to claim 34, wherein the housing includes a recess formed in the outer surface thereof, and wherein the plurality of activation switches and the nubs of the voltage divider network are disposed within the recess.

36. The electrosurgical pencil according to claim 1, wherein the at least one voltage divider network is rotatably supported on the housing.

37. An electrosurgical system, comprising:
a source of electro surgical energy;
an electrosurgical pencil selectively connectable to the source of electrosurgical energy, the electrosurgical pencil including:
an elongated housing;
an electrocautery electrode supported within the housing and extending distally from the housing, the electrocautery electrode being connected to the source of electrosurgical energy;
a plurality of activation switches supported on the housing, each activation switch being configured and adapted to selectively complete a control loop extending from the source of electrosurgical energy upon actuation thereof; and
at least one voltage divider network supported on the housing, the at least one voltage divider network being electrically connected to the source of electrosurgical energy for controlling the intensity of electrosurgical energy being delivered to the electrosurgical pencil.

38. The electrosurgical system according to claim 37, wherein the at least one voltage divider network further comprises:
a plurality of control wires electrically inter-connecting the respective activation switch to the source of electrosurgical energy, each control wire being isolated within the electrosurgical pencil from the control wire delivering electrosurgical energy to the electrocautery electrode.

39. The electrosurgical system according to claim 38, wherein the voltage divider network includes a slide operatively associated with the housing.

40. The electrosurgical system according to claim 39, wherein the plurality of activation switches define a first resistor network disposed within the housing, and wherein the slide defines a second resistor network disposed within the housing.

41. The electrosurgical system according to claim 40, wherein the slide simultaneously controls the intensity of electrosurgical energy delivered to the plurality of activation switches.

42. The electrosurgical system according to claim 41, wherein the electrosurgical pencil includes three mode activation switches supported on the housing, wherein each of the three mode activation switches is configured and adapted to deliver a characteristic signal to a source of electrosurgical energy which source of electrosurgical energy in turn transmits a corresponding waveform duty cycle to the end effector.

43. The electrosurgical system according to claim 42, wherein a first mode activation switch activates a waveform duty cycle which produces a dissecting effect, a second mode activation switch activates a waveform duty cycle which produces a dissecting and hemostatic effect, and a third mode activation switch activates a waveform duty cycle which produces a hemostatic effect.

44. The electrosurgical system according to claim 43, wherein the at least one voltage divider network includes a pair of nubs slidably supported on the housing, one each, on either side of the activation switches.

45. The electrosurgical system according to claim 44, wherein the at least one voltage divider network has a first position corresponding to a minimum intensity, a second position corresponding to a maximum intensity and a plurality of positions between the first and second positions corresponding to intensities between the minimum and the maximum intensity.

46. The electrosurgical system according to claim 45, wherein the at least one voltage divider network is configured and adapted to vary a current intensity from a minimum of about 60 mA to a maximum of about 240 mA at 2K ohms.

47. The electrosurgical system according to claim 46, wherein the at least one voltage divider network is configured and adapted to vary a current intensity from a minimum of about 100 mA to a maximum of about 200 mA.

48. The electrosurgical system according to claim 47, wherein the at least one voltage divider network is set to the minimum when the at least one voltage divider network is placed at a proximal-most position and is set to the maximum when placed at a distal-most position.

49. The electrosurgical system according to claim 48, wherein the at least one voltage divider network is set to the minimum when the at least one voltage divider network is placed at a distal-most position and is set to the maximum when placed at a proximal-most position.

50. The electrosurgical system according to claim 48, wherein the at least one voltage divider network is configured and adapted to provide a plurality of discreet intensity settings.

51. The electrosurgical system according to claim 48, wherein the at least one voltage divider network is configured and adapted to provide analog intensity settings.

52. The electrosurgical system according to claim 47, wherein the waveform duty cycle of the activation switches varies with a change in intensity produced by the at least one voltage divider network.

53. The electrosurgical system according to claim 41, wherein at least one activation switch is configured and adapted to control a waveform duty cycle to achieve a desired surgical intent.

54. The electrosurgical system according to claim 53, further including a molded hand grip operatively supported on the housing.

55. The electrosurgical system according to claim 54, wherein the hand grip is shaped and dimensioned to reduce fatigue on the hand of the user.

56. The electrosurgical system according to claim 54, wherein the hand grip provides traction to prevent movement of the pencil while changing the slide.

57. The electrosurgical system according to claim 53, further including three mode activation switches supported on the housing.

58. The electrosurgical system according to claim 57, wherein each mode activation switch delivers a characteristic signal to the source of electrosurgical energy which in turn transmits a corresponding waveform duty cycle to the electrocautery electrode.

59. The electrosurgical system according to claim 57, wherein a first activation switch delivers a first characteristic signal to the source of electrosurgical energy which in turn transmits a waveform duty cycle which produces a cutting effect, a second activation switch delivers a second characteristic signal to the source of electrosurgical energy which in turn transmits a waveform duty cycle which produces a blending effect, and wherein a third activation switch delivers a third characteristic signal to the source of electrosurgical energy which in turn transmits a waveform duty cycle which produces a coagulating effect.

60. The electrosurgical system according to claim 59, wherein an intensity controlling slide is supported in the housing.

61. The electrosurgical system according to claim 60, wherein each position on the slide delivers a characteristic signal to the source of electrosurgical energy which in turn adjusts the intensity of the waveform duty cycle corresponding to a particular activation switch.

62. The electrosurgical system according to claim 61, wherein the slide has a plurality of intensity settings.

63. The electrosurgical system according to claim 62, wherein the slide is configured and adapted to vary a current intensity from a minimum of about 60 mA to a maximum of about 240 mA at 2K ohms.

64. The electrosurgical system according to claim 62, wherein the slide is configured and adapted to vary a current intensity from a minimum of about 100 mA to a maximum of about 200 mA at 2K ohms.

65. The electrosurgical system according to claim 64, wherein the slide is set to a minimum when the potentiometer is placed at a first position and is set to a maximum when the potentiometer is placed at a second position.

66. The electrosurgical system according to claim 65, wherein the electrocautery electrode is one of a blade, needle, a loop and a ball.

67. The electrosurgical system according to claim 65, wherein the slide potentiometer includes a pair of nubs slidably supported, one each, on either side of the plurality of activation switches such that the potentiometer is operable from either side of the electrosurgical pencil.

68. The electrosurgical system according to claim 54, wherein the housing includes a recess formed in the outer surface thereof, and wherein the plurality of activation switches and the nubs of the voltage divider network are disposed within the recess.

69. The electrosurgical system according to claim 37, wherein the at least one voltage divider network is rotatably supported on the housing.

70. The electrosurgical system according to claim 37, wherein an intensity control slide is positioned on the body for each activation button.

71. The electrosurgical system according to claim 70, wherein each slide operates a voltage divider network, the voltage divider network produces a characteristic signal on a separate control wire to the source of electrosurgical energy.

* * * * *